(12) United States Patent
Spaulding et al.

(10) Patent No.: US 11,268,141 B2
(45) Date of Patent: Mar. 8, 2022

(54) METHODS FOR QUANTITATIVE AMPLIFICATION

(71) Applicants: BioFire Diagnostics, LLC, Salt Lake City, UT (US); BioFire Defense, LLC, Salt Lake City, UT (US)

(72) Inventors: Usha K. Spaulding, Murray, UT (US); Margarita Rogatcheva, Sandy, UT (US); Mark Aaron Poritz, Salt Lake City, UT (US); Robert John Crisp, Cottonwood Heights, UT (US)

(73) Assignees: BioFire Diagnostics, LLC, Salt Lake City, UT (US); BioFire Defence, LLC, Salt Lake City, UT (US)

( * ) Notice: Subject to any disclaimer, the term of this patent is extended or adjusted under 35 U.S.C. 154(b) by 531 days.

(21) Appl. No.: 16/087,724

(22) PCT Filed: Mar. 20, 2017

(86) PCT No.: PCT/US2017/023151
§ 371 (c)(1),
(2) Date: Sep. 24, 2018

(87) PCT Pub. No.: WO2017/165269
PCT Pub. Date: Sep. 28, 2017

(65) Prior Publication Data
US 2019/0078134 A1    Mar. 14, 2019

Related U.S. Application Data

(60) Provisional application No. 62/313,032, filed on Mar. 24, 2016.

(51) Int. Cl.
| | | |
|---|---|---|
| *C12Q 1/686* | (2018.01) | |
| *C12Q 1/6851* | (2018.01) | |
| *G16B 30/00* | (2019.01) | |
| *C07H 21/04* | (2006.01) | |
| *C12M 1/26* | (2006.01) | |
| *C12P 19/34* | (2006.01) | |
| *C12Q 1/6806* | (2018.01) | |
| *C12Q 1/70* | (2006.01) | |
| *C12Q 1/689* | (2018.01) | |

(52) U.S. Cl.
CPC ............. *C12Q 1/686* (2013.01); *C07H 21/04* (2013.01); *C12M 1/26* (2013.01); *C12P 19/34* (2013.01); *C12Q 1/6806* (2013.01); *C12Q 1/6851* (2013.01); *C12Q 1/70* (2013.01); *G16B 30/00* (2019.02); *C12Q 1/689* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 6,303,305 | B1 | 10/2001 | Wittwer et al. |
| 6,645,758 | B1 | 11/2003 | Schnipelsky et al. |
| 6,780,617 | B2 | 8/2004 | Chen |
| 7,387,887 | B2 | 6/2008 | Wittwer et al. |
| 8,024,132 | B2 | 9/2011 | Sagner et al. |
| 8,394,608 | B2 | 3/2013 | Ririe et al. |
| 8,744,777 | B2 | 6/2014 | Sagner et al. |
| 8,895,295 | B2 | 11/2014 | Ririe et al. |
| 2005/0014176 | A1 | 1/2005 | Swiger et al. |
| 2006/0292571 | A1 | 12/2006 | Babiel et al. |
| 2014/0038272 | A1 | 2/2014 | Ririe |
| 2014/0283945 | A1 | 9/2014 | Jones et al. |
| 2015/0118715 | A1 | 4/2015 | Wittwer et al. |
| 2015/0232916 | A1 | 8/2015 | Rasmussen et al. |
| 2017/0082628 | A1 | 3/2017 | Berek et al. |

FOREIGN PATENT DOCUMENTS

| | | |
|---|---|---|
| EP | 1319716 | 6/2003 |
| EP | 2406400 | 7/2016 |
| EP | 2598655 | 10/2016 |
| JP | 2006333821 A | 12/2006 |
| WO | 2007035475 | 3/2007 |
| WO | 2007061284 | 5/2007 |
| WO | 2017/044694 | 3/2017 |

OTHER PUBLICATIONS

Bio-Rad "Real-Time PCR: Applications Guide" product manual, bulletin 5279B, (95 pages) (2006).
International Search Report and the Written Opinion of the International Searching Authority corresponding to International Patent Application No. PCT/US2017/023151 (17 pages) (dated Aug. 28, 2017).
Extended European Search Report corresponding to European Patent Application No. 17770890.6 (10 pages) (dated Aug. 30, 2019).
Kalogianni et al. "Multiplex Quantitative Competitive Polymerase Chain Reaction Based on a Multianalyte Hybridization Assay Performed on Spectrally Encoded Microspheres" Analytical Chemistry, 79(17):6655-6661 (2007).
"LightCycler 480 Instrument Absolute Quantification Quick Reference Card" (4 pages) (2010).
Nygren et al. "Quantification of HIV-1 Using Multiple Quantitative Polymerase Chain Reaction Standards and Bioluminometric Detection" Analytical Biochemistry, 288:28-38 (2001).
International Preliminary Report on Patentability corresponding to International Patent Application No. PCT/US2017/023151 (30 pages) (Corrected Version dated May 11, 2020).

*Primary Examiner* — Joseph Woitach
(74) *Attorney, Agent, or Firm* — Myers Bigel, P.A.

(57) ABSTRACT

Methods, sample vessels, and instruments are provided for quantitative and semi-quantitative amplification.

26 Claims, 13 Drawing Sheets

```
┌─────────────────────────────────────────────┐
│       SPC (PHiX) CALIBRATION WITH CMV       │
│   SYNTHETIC QUANTIFICATION STANDARDS        │
│   - 4 DILUTIONS OF SPC TO BE CALIBRATED     │
└─────────────────────────────────────────────┘
```

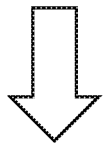

```
┌─────────────────────────────────┐
│     CHOICE OF THE OPTIMUM       │
│         SPC DILUTION            │
└─────────────────────────────────┘
```

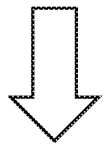

```
┌─────────────────────────────────────────────────────┐
│ QUANTIFICATION WITH THE "ADJUSTER" (SPC OR QS3)     │
│ 4 RUNS ON 2 DIFFERENT INSTRUMENTS                   │
│  • 4 DILUTIONS OF AD169 SPIKED IN WHOLE BLOOD TESTED│
│    IN 4 REPLICATES                                  │
│  • 1 INHIBITED SAMPLE                               │
│  • 2QCMD WHOLE BLOOD SAMPLES                        │
│  • 5 WHOLE BLOOD CLINICAL SAMPLES                   │
└─────────────────────────────────────────────────────┘
```

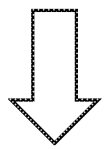

```
┌─────────────┐
│   ANALYZE   │
└─────────────┘
```

*FIG. 12*

METHODS FOR QUANTITATIVE AMPLIFICATION

STATEMENT OF PRIORITY

This application is a 35 U.S.C. § 371 national phase application of International Application Serial No. PCT/US2017/023151, filed Mar. 20, 2017, which claims the benefit, under 35 U.S.C. § 119(e), of U.S. Provisional Application Ser. No. 62/313,032, filed Mar. 24, 2016, the entire contents of each of which are incorporated by reference herein.

BACKGROUND

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays to be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases, there is inadequate sample to assay for all possible etiological agents. A solution is to run "multiplex PCR" wherein the sample is concurrently assayed for multiple targets in a single reaction. While multiplex PCR has proven to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product often increases robustness. However, this further handling can be expensive and may lead to contamination or other problems.

Fully integrated multiplex PCR systems integrating sample preparation, amplification, detection, and analysis are user friendly and are particularly well adapted for the diagnostic market and for syndromic approaches. The FilmArray® (BioFire Diagnostics, LLC, Salt Lake City, Utah) is such a system, a user friendly, highly multiplexed PCR system developed for the diagnostic market. The single sample instrument accepts a disposable "pouch" that integrates sample preparation and nested multiplex PCR. Integrated sample preparation provides ease-of-use, while the highly multiplexed PCR provides both the sensitivity of PCR and the ability to test for up to 30 different organisms simultaneously. This system is well suited to pathogen identification where a number of different pathogens all manifest similar clinical symptoms. Current available diagnostic panels include a respiratory panel for upper respiratory infections, a blood culture panel for blood stream infections, a gastrointestinal panel for GI infections, and a meningitis panel for cerebrospinal fluid infections. Other panels are in development.

Many of the pathogens targeted by FilmArray panels, as well as other detection systems, can be found in the environment and as commensals at the site of sample collection. For example, in diseases such as pneumonia, the most frequently encountered bacterial pathogens may also exist as "normal flora" of the oropharyngeal passage which is often itself the site of sample collection (sputum and tracheal aspirates or nasopharyngeal swab (NPS)) or the route for collection of more invasive specimens such as bronchoalveolar lavage (BAL). Frequent contamination by or co-collection of normal flora is unavoidable in such cases. Hence, the established practice in microbiological laboratories is to perform semi-quantitative or quantitative cultures to distinguish pathogenic loads of bacteria from non-clinically relevant commensal carriage. Different diagnostic titer guidelines exist for different types of specimens. Quantitative PCR (qPCR) can function as a rapid and objective molecular alternative to the time-consuming and often subjective microbiological methods.

Absolute quantification, including amplification by qPCR, frequently uses a standard curve approach. In this approach, a standard curve generated from plotting the crossing point (Cp) values obtained from real-time PCR against known quantities of a single reference template provides a regression line that can be used to extrapolate the quantities of the same target gene in samples of interest. Serial dilutions (illustratively 10-fold dilutions) of the reference template are set up alongside samples containing the specific gene target that needs to be quantified. Various separate reactions are run, usually one for each level of the reference target and one each for the samples of interest. Also, since assay-specific differences in PCR efficiencies often affect quantification, separate standard curves, with separate reference templates, are set up to quantify different gene targets.

However, using this approach to quantify targets in a multiplexed PCR scenario can be challenging. Although quantification of targets from multiplexed PCR has been performed, this approach requires setting up multiple individual PCR standard curves for each assay included in the multiplex (Phillips et al 2014). Also, this approach assumes or requires the assays to have the same PCR efficiency in singleplex and multiplex reactions. All standard curve-based quantification approaches published to date require the setting up of external standard curves where the different levels of reference templates are added to separate reaction chambers.

This approach is not readily available in a system such as the multiplexed FilmArray platform, where a single test is designed to provide a sample-to-answer solution. The FilmArray system employs a two-stage nested-multiplex PCR where only a single chamber is available for the first-stage multiplex reactions. Therefore, external standard curves for each PCR assay cannot be included. Also, in a single chamber reaction, one cannot easily keep the serial dilutions of reference templates separate in order to obtain Cp values for each level. Additionally, since nucleic acid purification from a patient sample is integrated into the FilmArray system, the effect of sample-driven variability in nucleic acid extraction, as well as the effect of any sample-derived inhibitors on PCR, and thus quantification, cannot be estimated easily by an external standard curve. This disclosure provides methods, systems, and kits for generating an internal standard curve in a multiplex reaction that can provide simultaneous quantification of multiple target species that also takes into account the effects of assay-specific and matrix-derived variances in PCR outcomes. This disclosure also teaches use of process controls or sample processing control(s) for quantification.

BRIEF SUMMARY

In one aspect of the present disclosure, methods of performing quantitative two-step amplification on a sample are provided, the methods comprising amplifying the sample in a first-stage multiplex amplification mixture, the amplification mixture comprising a plurality of target primers, each target primer configured to amplify a different target that may be present in the sample, the amplification mixture further comprising a plurality of internal quantification standard nucleic acids each provided at a different known concentration and at least one quantification standard primer, the quantification standard primer configured to amplify quantification standard nucleic acids, dividing the first-stage amplification mixture into a plurality of second-stage individual reactions, a first group of the plurality of second-stage reactions each comprising at least one primer configured to further amplify one of the different targets that may be present in the sample, and a second group of the plurality of second-stage reactions each comprising at least one primers configured to further amplify one of the quantification standard nucleic acids, and subjecting the plurality of second-stage individual reactions to amplification conditions to generate one or more target amplicons and a plurality of quantification standard amplicons.

In another aspect of this disclosure, methods of performing quantitative PCR on a sample are provided, the methods comprising amplifying the sample in an amplification mixture, the amplification mixture comprising a pair of target primers configured to amplify a target that may be present in the sample, the amplification mixture further comprising a plurality of quantification standard nucleic acids each provided at a different known concentration and at least one pair of quantification standard primers, the quantification standard primers configured to amplify quantification standard nucleic acids, generating a standard curve from the quantification standard amplicons, and quantifying the target nucleic acid using the standard curve.

In yet another aspect of this disclosure, methods for performing quantitative nucleic acid amplification on a sample are provided, the methods comprising: a) lysing said sample; b) extracting the nucleic acid molecules from said sample; c) performing nucleic acid amplification; wherein a microorganism is added to said sample prior to or during step a) in a known amount as a sample processing control; characterized in that a nucleic acid sequence from the sample processing control serves as a quantification standard. Uses of a sample processing control as a quantification standard in a method for quantifying a nucleic acid in a sample are also provided.

In still another aspect of this disclosure, sample vessels for performing quantitative two-step PCR on a sample are provided, the sample vessels comprising an amplification container comprising a plurality of pairs of target primers, each pair of target primers configured to amplify a different target that may be present in the sample, the amplification mixture further comprising a plurality of internal quantification standard nucleic acids each provided at a different known concentration and at least one pair of calibrator primers, the calibrator primers configured to amplify calibrator nucleic acids, and a plurality of second-stage individual reaction wells, a first group of the plurality of second-stage reaction wells each comprising a pair of primers configured to further amplify one of the different targets that may be present in the sample, and a second group of the plurality of second-stage reactions each comprising a pair of primers configured to further amplify one of the calibrator nucleic acids.

In yet another aspect of this disclosure, methods are provided for testing a sample processing method, comprising adding a quantification standard to a sample in a known amount; extracting nucleic acids from the sample using the sample processing method; adding a second quantification standard to the sample in a second known amount; performing nucleic acid amplification of the nucleic acids and the quantification standards; and determining a difference between amplification of the quantification standard and the second quantification standard; wherein the difference is indicative of efficiency of the sample processing method.

In one more aspect of this disclosure, instruments for performing quantitative two-step PCR on a sample are provided, comprising an opening for receiving the sample vessel as disclosed herein, a first heater for subjecting the amplification container to amplification conditions, a second heater for subjecting the plurality of second-stage individual reaction wells to amplification conditions, a computer programmed to generate a standard curve using the amplification of the quantification standard nucleic acids and output a quantitative or semi-quantitative result for each amplified target.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 12 is a flow chart of the experiment design of Example 5.

DETAILED DESCRIPTION

Figure 1:
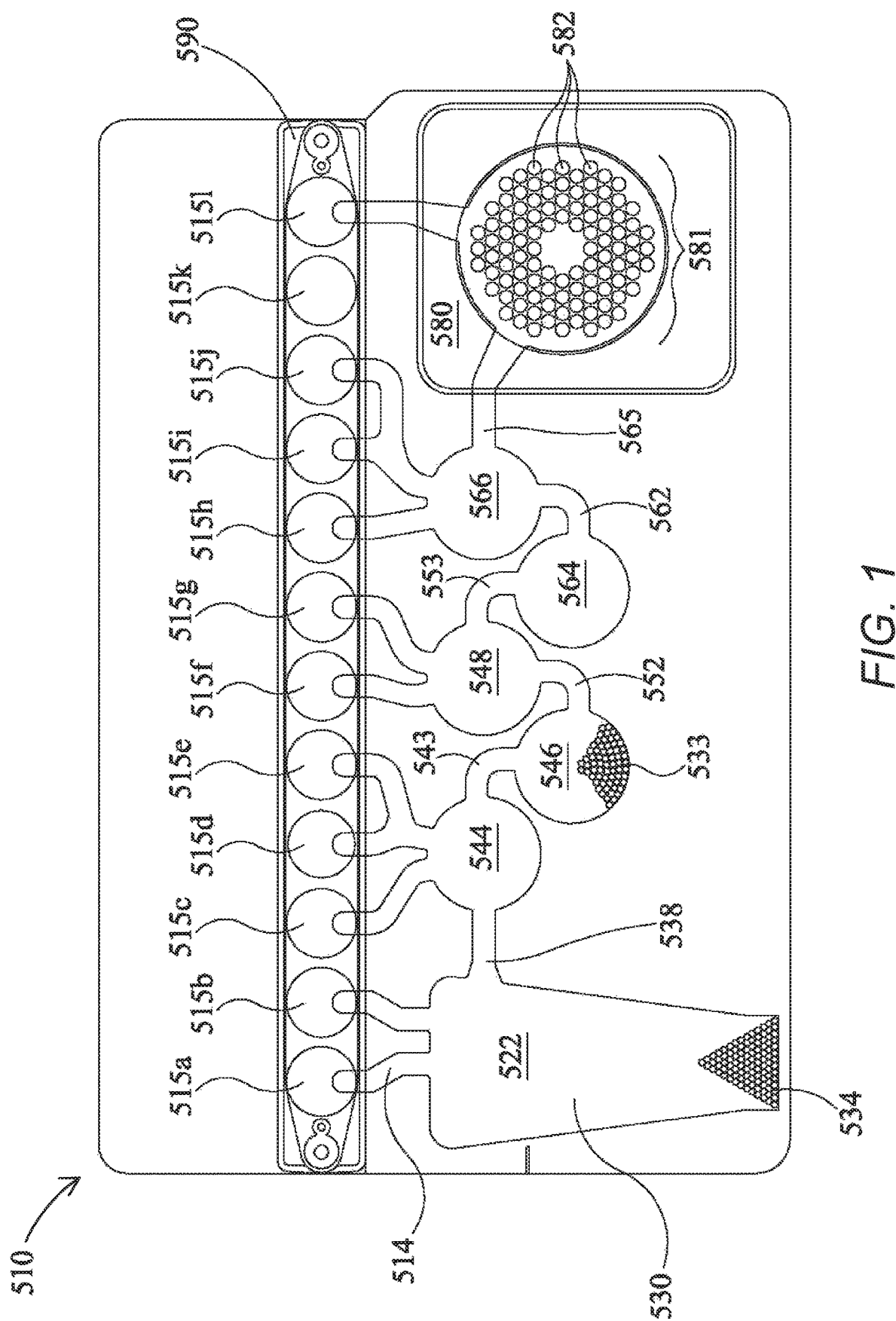
FIG. 1 shows a flexible pouch according to one embodiment of the present invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g., a polypeptide or nucleic acid); or a solution containing a non-naturally occurring nucleic acid illustratively a cDNA or next-generation sequencing library, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), modified or treated bases and non-phosphodiester internucleoside linkages (e.g., peptide nucleic acid (PNA) or thiodiester linkages). In particular, nucleic acids can include, without limitation, DNA, cDNA, gDNA, ssDNA, dsDNA, RNA, including all RNA types such as miRNA, mtRNA, rRNA, including coding or non-coding regions, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured. As a probe, the oligonucleotide could be used as part of many fluorescent PCR primer- and probe-based chemistries that are known in the art, including those sharing the use of fluorescence quenching and/or fluorescence resonance energy transfer (FRET) configurations, such as 5'nuclease probes (TaqMan® probes), dual hybridization probes (HybProbes®), or Eclipse® probes or molecular beacons, or Amplifluor® assays, such as Scorpions®, LUX® or QZyme® PCR primers, including those with natural or modified bases.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant at about melting temperature (Tm) minus 5° C. (i.e., 5° below the Tm of the nucleic acid). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR) of any type (single-step, two-steps, or others); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), next generation sequencing techniques, and the like. Therefore, when the term PCR is used, it should be understood to include other alternative amplification methods, including amino acid quantification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

By "sample processing control" is meant a pathogen, microorganism, cell, whether living or not, nucleic acid, or any particle, natural or synthetic, possessing the ability to mimic a pathogen or a portion of it, or a nucleic acid, and its behavior during the workflow of the sample. A sample processing control is often included in the device in a known amount to control some or all of the steps of the workflow followed by the sample, illustratively to ensure that the sample has been correctly lysed, the nucleic acids of the potentially infecting target pathogens have been correctly extracted and purified, and that correct amplification and detection of specific sequences of target pathogens has taken place.

Illustratively, a microorganism (illustratively *Schizosaccharomyces pombe* (*S. pombe*)) that is used as sample processing control mimics as closely as possible the target microorganisms to be detected and quantified. The sample processing control particle may reproduce the structure (such as membrane(s) and/or capsid and/or envelop) of the pathogens to be detected, allowing it to mimic the behavior of the pathogen and its target nucleic acids along the workflow. The goal of the sample process control is to ensure that the lysis and nucleic acid extraction yield of the target are similar to the yield of the sample processing control, and that the purified nucleic acids are processed appropriately to ensure an optimal amplification/detection. For qualitative results, a pathogen can be reported as positive or negative, or may be reported as undetermined if a run control failed. The sample processing control may be one of several run controls and should be positive, and perhaps be within a specified range, to validate the run, since some inhibitory conditions can decrease the yield of extraction, purification, or PCR amplification/detection. The sample processing control can be used to monitor this kind of inhibition, the reduction of the yield being similar between the sample processing control and the target pathogen. For qualitative results, such inhibition, if undetected, can lead to a false negative result. For quantitative results, an inhibition of one of the steps of the workflow can provide an underestimated quantification result. Therefore, several illustrative embodiments of the present invention use at least one sample processing control (SPC) for at least two goals:

1) to control and validate the workflow: the classic role of the SPC as described above, and
2) to aid in the quantification of a targeted nucleic acid(s) in a tested sample: a new role of the SPC that is also used as quantification standard.

Illustratively, the SPC follows some or all of the process to which the sample is subjected. Thus, the SPC may be added prior to or during the step of lysis of the sample. The sample processing control may be chosen based on the type of target pathogen(s). For example, a bacteriophage as the PhiX 174 can be chosen for an assay focused on viruses, a bacteriophage being a good candidate to mimic the target viruses, or a yeast, such as *S. pombe*, for use in a broad bacteria and yeast quantification assay.

If a single pathogen is to be detected, the two amplification assays, illustratively PCR assays (target pathogen and sample processing control used as a quantification standard) can be designed to reach the same or similar thermodynamics characteristics and enable an accurate quantification (as in Example 5) using a synthetic quantification standard.

For the quantification of multiple pathogens (i.e., multiplex amplification), it can be difficult to fit the amplification protocols, illustratively the PCR design, of the sample processing control, with the protocol of the amplification assay, illustratively a PCR assay for each pathogen, to obtain the same thermodynamics characteristics, illustratively because of sequence variability and amplicon length. As a consequence, the PCR efficiencies of the different target pathogens may be different. For this purpose, a correction factor can be calculated for each pathogen that correlates the quantification obtained with the quantification standard and the imported standard curve.

In an alternative to the synthetic quantification standard, the calibration could be performed against a known natural microorganism with known concentrations or against other naturally occurring nucleic acid templates.

In another embodiment of the invention, it is also possible to have reliable quantification of a pathogen in any amplification system with at least two different, illustratively three or four different sample processing controls, provided that these sample processing controls could be identified via a known technique of identification such as sequence-specific probes that are labeled fluorescently, radioactively, chemiluminescently, enzymatically, or the like, as are known in the art.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such instruments and pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. Such amplification systems may include a single multiplex step in an amplification container and may optionally include a plurality of second-stage individual or lower-order multiplex reactions in a plurality of individual reaction wells. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington Del.) of about 0.0048 inch (0.1219 mm) thick and polypropylene films of 0.001-0.003 inch (0.025-0.076 mm) thick perform well. Illustratively, pouch 510 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material.

Illustratively, a plastic film is used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components.

Pouch 510 may be used in a manner similar to that described in U.S. Pat. No. 8,895,295. In one illustrative embodiment, a 300 µl mixture comprising the sample to be tested (100 µl) and lysis buffer (200 µl) is injected into an injection port (not shown) in fitment 590 near entry channel 515a, and the sample mixture is drawn into entry channel 515a. Water is also injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed.

For more information on various configurations of pouch 510 and fitment 590, see U.S. Pat. No. 8,895,295, already incorporated by reference.

After injection, the sample is moved from injection channel 515a to lysis blister 522 via channel 514. Lysis blister 522 is provided with beads or particles 534, such as ceramic beads, and is configured for vortexing via impaction using rotating blades or paddles provided within the FilmArray® instrument. Bead-milling, by shaking or vortexing the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2A:
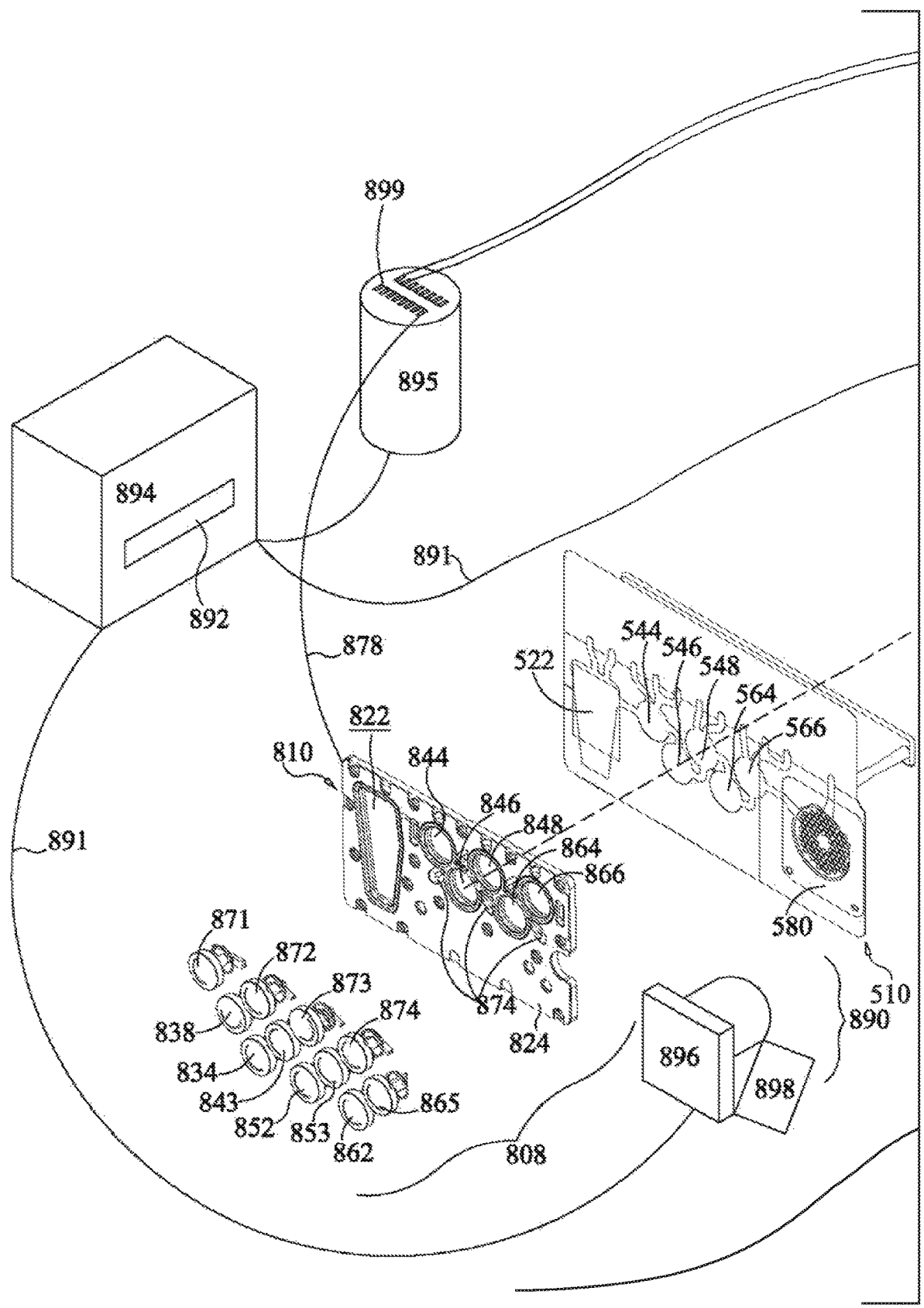
FIGS. 2A-B together form an exploded perspective view of an instrument for use with the pouch of FIG. 1, including the pouch of FIG. 1, according to an example embodiment of the present invention.
Figure 2B:
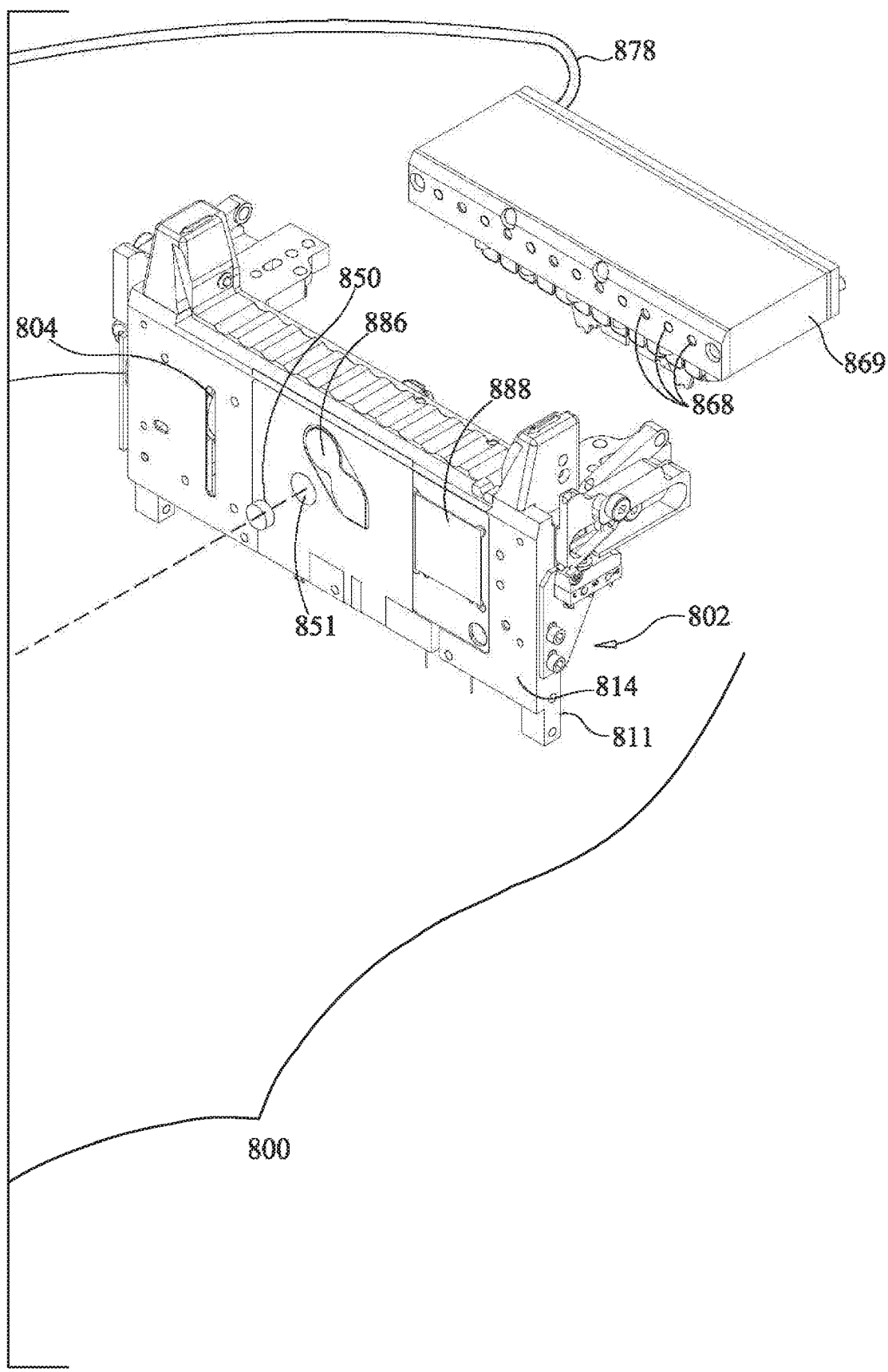
Figure 4:
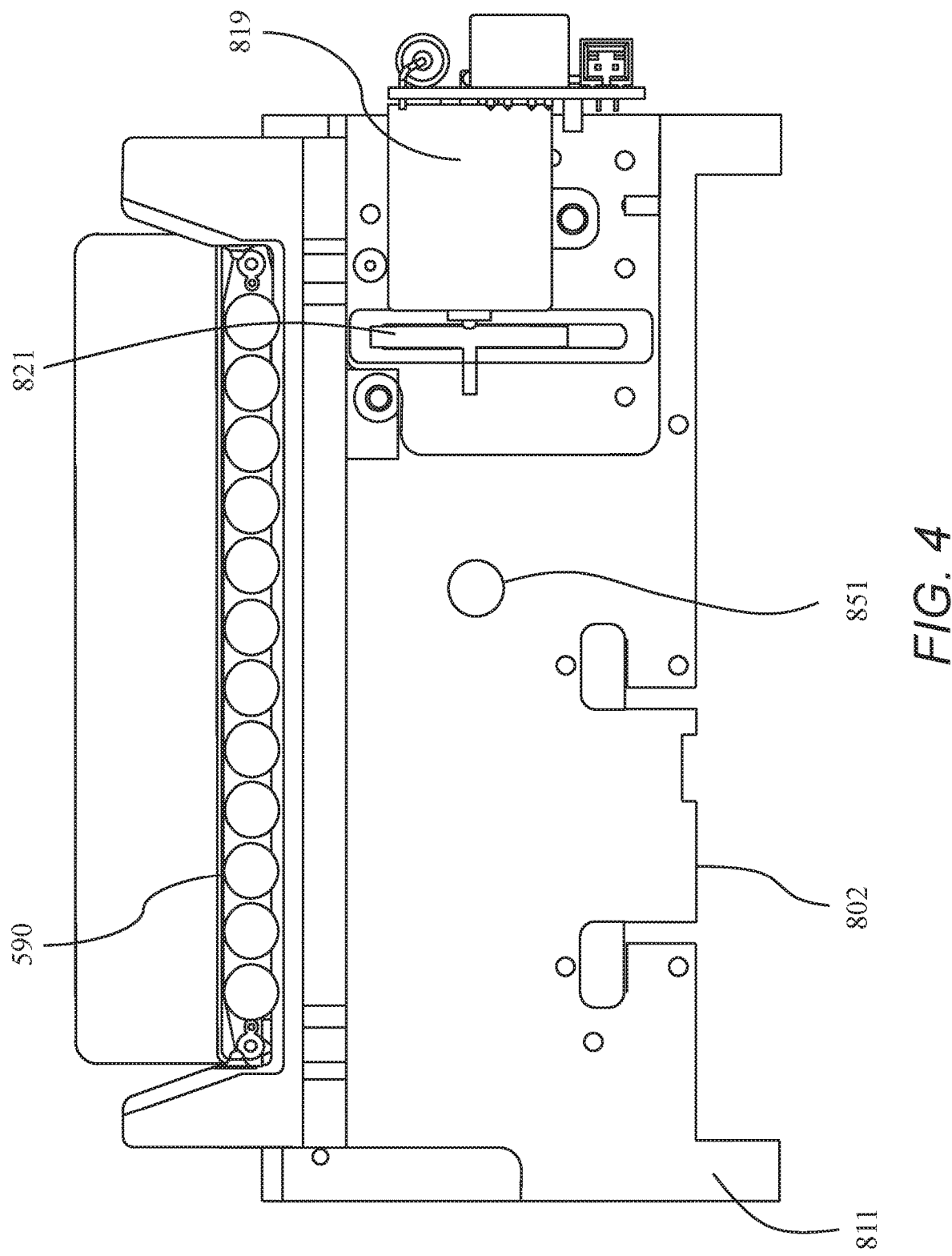
FIG. 4 shows a motor used in one illustrative embodiment of the instrument of FIG. 2B.

FIG. 4 shows a bead beating motor 819, comprising blades 821 that may be mounted on a first side 811 of support member 802, of instrument 800 shown in FIGS. 2A-B. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample.

Once the cells have been adequately lysed, the sample is moved through channel 538, blister 544, and channel 543, to blister 546, where the sample is mixed with a nucleic acid-binding substance, such as silica-coated magnetic beads 533. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, a reverse-transcription (RT) step may be performed prior to or simultaneously with the first-stage multiplex PCR. First-stage multiplex PCR temperature cycling in the FilmArray® instrument is illustratively performed for 15-30 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair (or sometimes multiple pairs of primers). If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
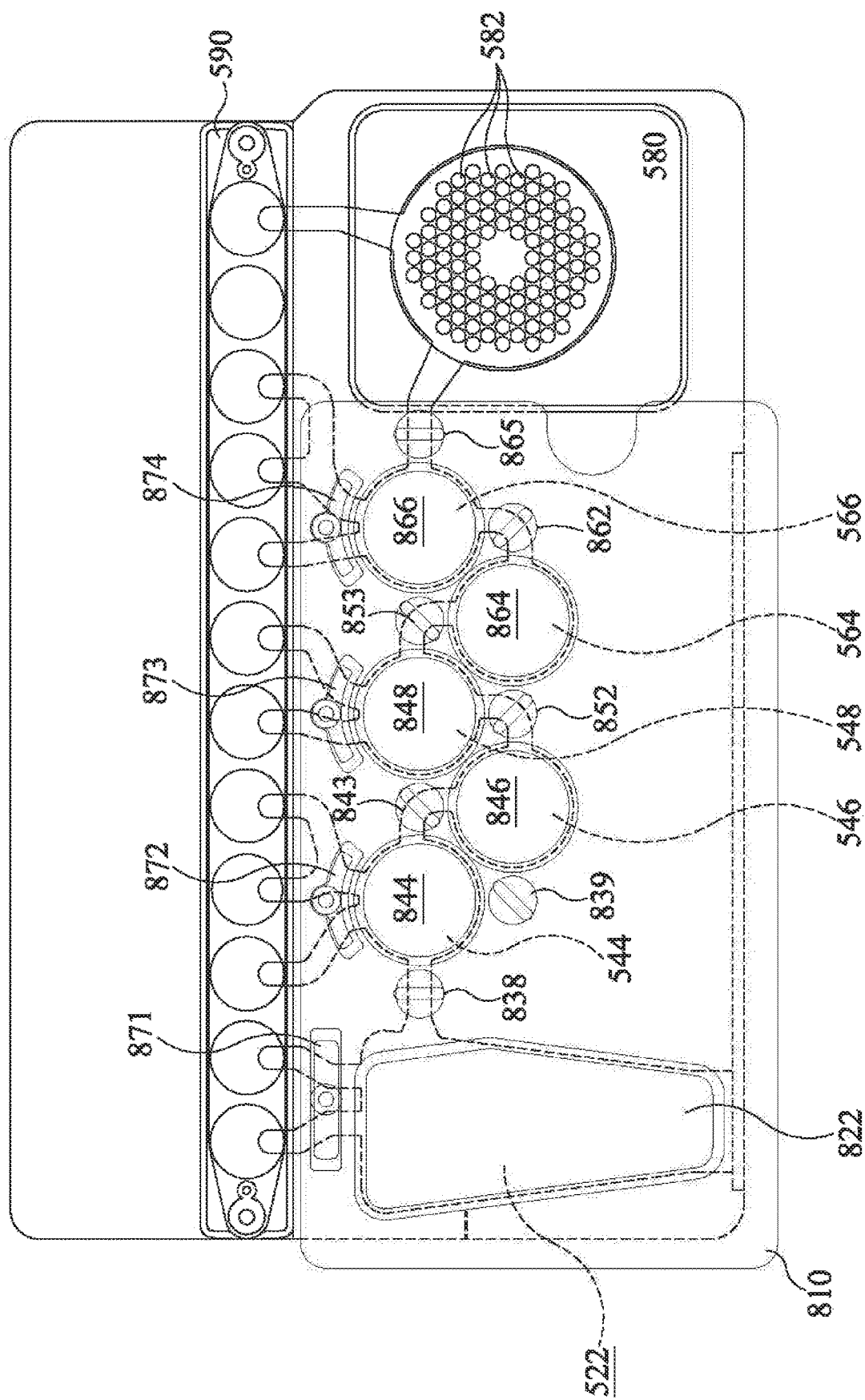
FIG. 3 shows a partial cross-sectional view of the instrument of FIGS. 2A-B, including the bladder components of FIG. 2A, with the pouch of FIG. 1 shown in dashed lines, according to an example embodiment of the present invention.

When pneumatic pressure is used to move materials within pouch 510, in one embodiment a "bladder" may be employed. The bladder assembly 810, a portion of which is shown in FIGS. 2A-B and 3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification and single-stage PCR, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2A-B and 3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned in one or two dimensions such that a small number of actuators could be used for several of the processing stations including sample disruption, nucleic-acid capture, first and second-stage PCR, and other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Other prior art instruments teach PCR within a sealed flexible container. See, e.g., U.S. Pat. Nos. 6,645,758 and 6,780,617, and U.S. Patent Application No. 2014/0038272, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

FIGS. 2A-B show an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Bladder plate 810, with bladders 822, 844, 846, 848, 864, 866, hard seals 838, 843, 852, 853, seals 871, 872, 873, 874 form bladder assembly 808 may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Each pneumatic actuator is connected to compressed air source 895 via valves 899. While only several hoses 878 are shown in FIGS. 2A-B, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Assembly 808 is illustratively mounted on a movable support member, although it is understood that other configurations are possible.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of heating/cooling devices, illustratively Peltier heaters, are mounted on a second side 814 of support 802. First-stage heater 886 is positioned to heat and cool the contents of blister 564 for first-stage PCR. Second-stage heater 888 is positioned to heat and cool the contents of second-stage blisters 582 of pouch 510, for second-stage PCR. It is understood, however, that these heaters could also be used for other heating purposes, and that other heaters may be use, as appropriate for the particular application. Other configurations are possible.

When fluorescent detection is desired, an optical array 890 may be provided. As shown in FIGS. 2A-B, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, may calculate amplification curves, melting curves, Cps, Cts, standard curves, and other related data, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, Utah) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophda pneumoniae*, and *Mycoplasma pneumoniae*. The high density array 581 is able to accommodate such a panel in a single pouch 510. Other panels are available for the FilmArray®, each assaying for at least 20 pathogens.

The illustrative second-stage PCR master mix contains the dsDNA binding dye LCGreen® Plus to generate a signal indicative of amplification. However, it is understood that this dye is illustrative only, and that other signals may be used, including other dsDNA binding dyes, and probes that are labeled fluorescently, radioactively, chemiluminescently, enzymatically, or the like, as are known in the art.

The illustrative FilmArray instrument is programmed to make positive or negative calls for each second-stage reaction based on a post-PCR melt. The melt curve must produce a melt peak (first derivative maximum or negative first derivative maximum) within a pre-defined temperature range, for the call to be positive. It is understood that this method of calling each second-stage reaction is illustrative only, and that calls could be made using real-time amplification data or by other means, as are known in the art.

Example 2—Designing Quantification Standards for Multiplex PCR

In systems such as the FilmArray where a single multiplex PCR is performed in one reaction chamber, it is not convenient to generate standard curves using 10-fold dilutions of a single reference template, since the individual levels cannot be distinguished easily. For example, if a single reference template is added into the single first-stage reaction chamber at concentrations of 10 copies, 100 copies and 1000 copies, the final concentration of the reference template in that chamber will be 1110 copies, and absent some other label, the individual dilutions are not distinguishable. Furthermore, in a two-step multiplex PCR system, standard curves generated solely in the nested second-stage PCR may be of limited value for quantification, as single-plex standard template amplification reactions may not accurately reflect all of the upstream manipulations that the sample undergoes or may not be amplified with similar efficiencies, and, therefore, may not be reflective of the entire process.

In this illustrative example, different nucleic acid templates (illustratively varying in sequence and/or length), illustratively synthetic quantification standards, are used to represent different levels of a dilution series. In one illustrative embodiment, assays for all of the synthetic quantification standards have similar amplification efficiency and produce the same or similar Cp values at each given dilution point in the multiplex setting. Illustratively, all target assays, are optimized for the same performance characteristics, including efficiency, although corrections may be applied to adjust for assay-specific variation in efficiency.

In one illustrative example, outer and inner amplicon sizes for the quantification standards may be representative of amplicon sizes for the quantitative target assays. Also, the sequence or GC content may be the same or similar in between the priming regions. Illustratively, the sequences may be identical with an exception of at least one inner priming region, which should be different enough to avoid cross-reactivity between inner assays. If sequences differ only by inner primer binding region, then the same PCR1 primers may be used to amplify all quantification standards, thus minimizing potential differences in the PCR1 assays performances. Moreover, if labels are used, the sequences may be identical, and if labels are not used, even a slight difference in sequence can provide for detection, illustratively in a second-stage single-plex reaction. However, it is understood that these parameters are illustrative only, and other means for detection and controlling amplification efficiencies are possible. It is understood that quantification standards present in the multiplex reaction should be designed to match reaction parameters, such as $Mg^{2+}$, primer concentration, Tm, and cycling conditions. It is also understood that it is desirable to minimize non-specific amplification of the synthetic templates in the multiplex PCR reaction.

Figure 5:
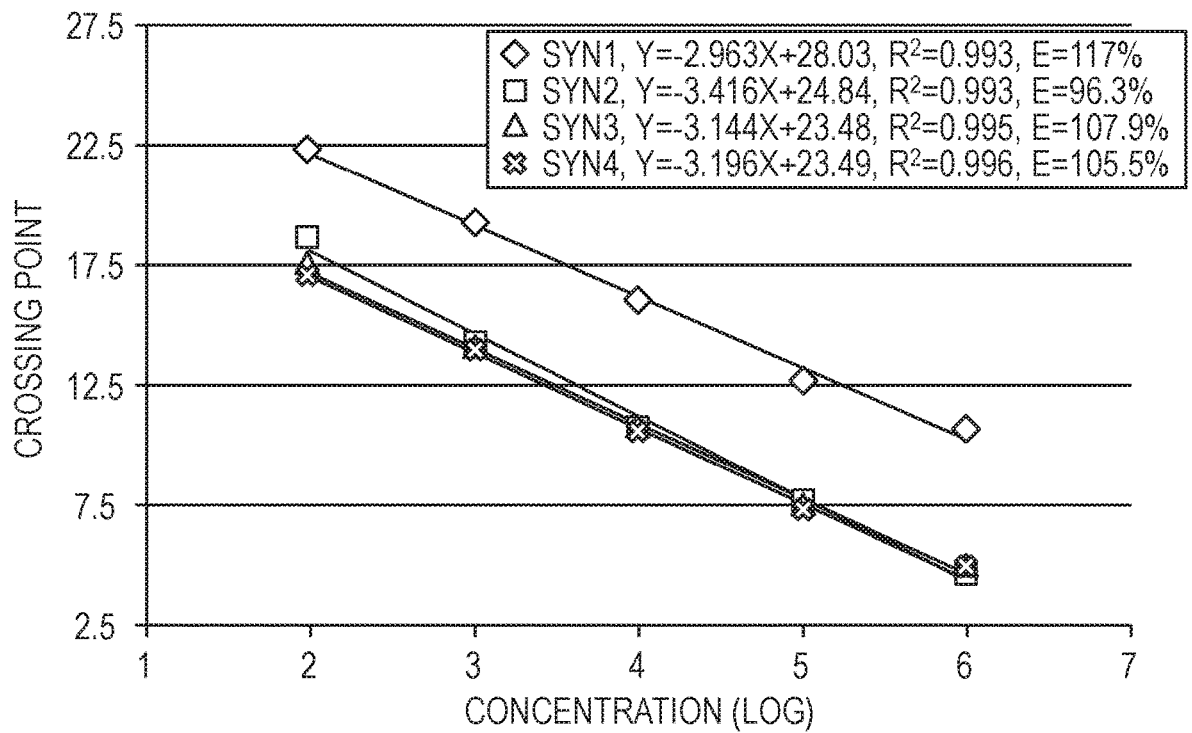
FIG. 5 shows the Cp across five dilutions of four different prospective synthetic quantification standards.

FIG. 5 shows Cp vs. concentration of four prospective internal quantification standards. In this illustrative embodiment, the internal quantification standards have synthetic sequences. In this illustrative example, for the second-stage inner reaction, the four quantification standards all share one common primer and each has one unique specific primer. They were also designed to share both outer primers for first-stage PCR. Thus, each of the second-stage wells used for detecting the quantification standards would be spotted with the common primer and the primer for that quantification standard, such that only one quantification standard should amplify in each such well. However, it is understood that this is an illustrative example only, and that other configurations are possible. Syn2, Syn3, and Syn4 each have similar amplification efficiencies and were chosen for additional study. Syn1 behaves differently and was omitted from further work. Thus, in one embodiment it is desirable to have multiple quantification standards that have similar amplification efficiencies.

In this illustrative example, amplification was detected using the dsDNA binding dye LCGreen Plus. However, this is illustrative only and other dsDNA binding dyes, probes, signals, or other ways of detecting amplification are within the scope of this invention.

It is understood that there are various ways of designing quantification standards that have similar amplification efficiencies. In one embodiment, the quantification standards have the same sequence between the inner primers and differ only in inner primer binding sequence. In another embodiment, the quantification standards are all of substantially the same length and substantially the same GC content. In yet another embodiment, the sequences are of differing lengths but also differ in GC content to compensate. Other ways of designing nucleic acids with similar amplification efficiencies are known in the art.

In one embodiment, illustratively when the quantification standards are used in a two-step nested multiplex PCR reaction, the quantification standards may all use the same outer primers in the first-stage PCR reaction, potentially even sharing identical regions surrounding primers to avoid differences due to the secondary structure formations. The quantification standards may then be distinguished by using different inner primers in the individual second-stage PCR reactions, either with each calibrator having a unique pair of inner primers, or, as above, sharing one inner primer and having one unique inner primer. Such an embodiment has advantages in that each of the quantification standards binds to its first-stage primers with the same kinetics, and the complexity of the first-stage multiplex PCR reaction may be minimized.

While reference is made to two-step PCR, the same principle can be used in a single-step multiplex PCR. In this case, the quantification standards may have different forward or reverse primers or the same forward and reverse primers and illustratively each has a specific fluorescent probe or other identifiable label, such as chemiluminescence, bioluminescence, radioluminescence, electroluminescence, electrochemiluminescence, mechanoluminescence, crystalloluminescence, thermoluminescence, sonoluminescence, phosphorescence and other forms of photoluminescence, enzymatic, radioactive, and the like are contemplated herein. The application is only limited by the number of detection channels available in any system or other methods for distinguishing the labels, as are known in the art. Some labels may require post-amplification processing. Further, it is understood that labeled quantification standards may be used in a two-step PCR wherein the same or different primer sequences may be used and the label is used to detect in the second-stage PCR. In such an embodiment, the labeled quantification standards optionally may be multiplexed in the second-stage PCR and distinguished by the label.

While synthetic quantification standards are used in this example, it is understood that the sequences used for quantification standards may be natural occurring. For example, if yeast is used as the SPC, yeast sequences may be used for one or more of the quantification standard sequences. For the fission yeast *Schizosaccharomyces pombe*, the Tf2-type retrotransposable element/transposon is present in 13 copies while the ribosomal RNA genes is repeated 47 times. In another example, gene sequences that exist in different copy numbers may be used. Illustratively, fungal pathogens have 50 to 200 copies of the ribosomal RNA gene per nuclear genome. These pathogens also have transposons that vary between five and 20 copies per genome. Bacterial pathogens have between 1 and 15 copies per genome but most have more than 5 copies. Other naturally occurring or synthetic templates may be used, such as bacteriophages for viruses and synthetic particles able to mimic membrane and/or capsid and/or envelope structures. Moreover, while three quantification standards are used in many of the examples herein, it is understood that only two quantification standards are needed to define a linear standard curve, and more quantification standards may be desired in embodiments where a wide range of target concentrations is expected or where a non-linear standard curve is expected. Illustratively, the number of quantification standards may be chosen based on the dynamic range of the system and the requirements of the assay.

Alternatively, as shown in Example 5, it is also possible to use only one quantification standard (see the sample processing control (SPC) discussed in Example 5) in each experimental run and to rely on an imported standard curve for the quantification previously generated with a quantification standard range, illustratively with at least 3 quantification standards (named QS in Example 5) which may be included in software for this analysis.

Example 3—Multiplex Calibration

Figure 6A:
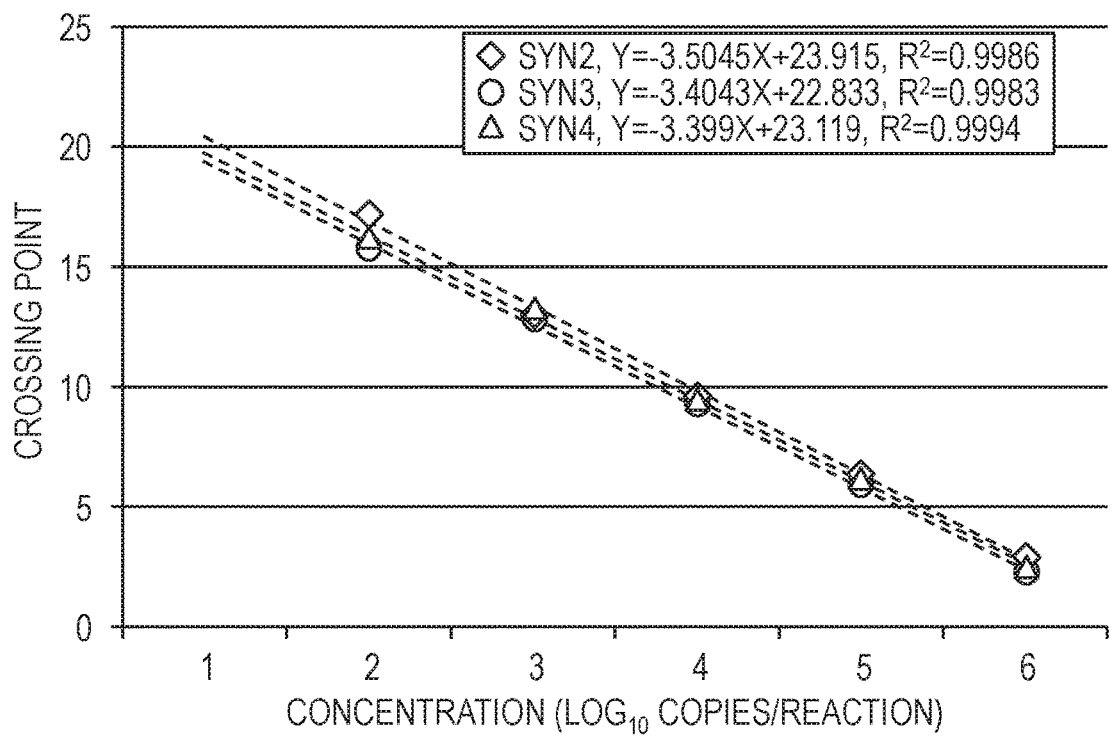
FIG. 6A is similar to FIG. 5, but showing data for only three of the quantification standards.
Figure 6B:
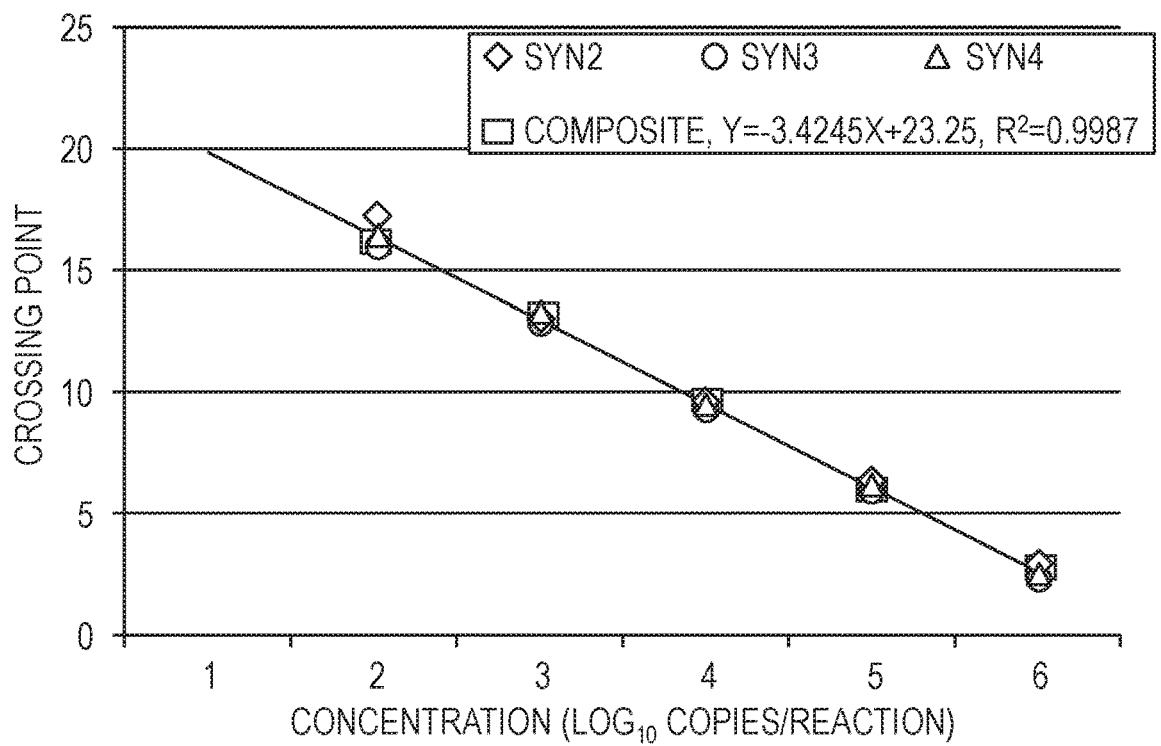
FIG. 6B shows a single curve using the data from all three of the quantification standards.

FIG. 6A is similar to FIG. 5, but showing data only from the three chosen calibrator sequences. FIG. 6A demonstrates the linearity and nearly identical amplification efficiencies for the three illustrative quantification standards. FIG. 6B shows a composite standard curve generated from the combination of three points each of the three quantification standards over a total of five dilutions.

Figure 7:
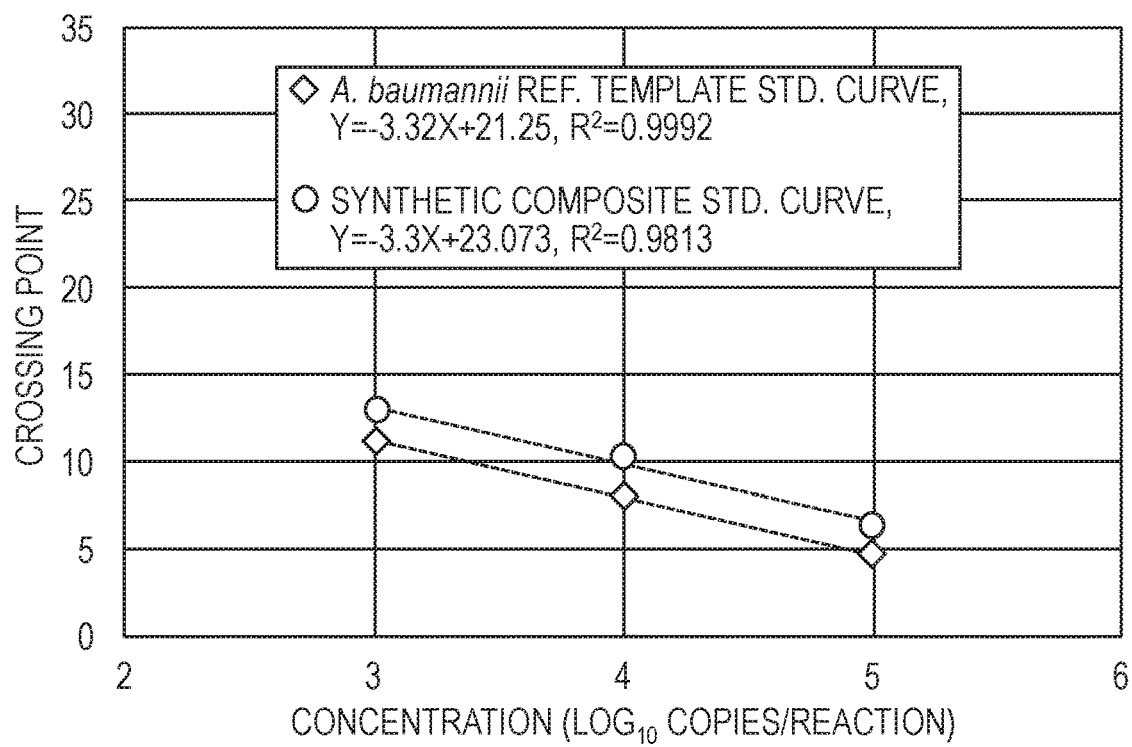
FIG. 7 shows a standard curve for *A. baumannii* plotted along with a curve generated from the three quantification standards. The x-axis is the amount of *A. baumannii* or quantification standards included in the reaction, and the y-axis is the Cp.

Now that the illustrative calibration plot has been generated, a standard curve using assay-specific reference templates for each target assay may be generated. FIG. 7 compares the externally generated standard curve using a well-quantified synthetic reference template for *Acinetobacter baumannii* with a composite internal standard curve generated using the quantification standards. Here the three "Syn" templates were pre-mixed before addition to the reaction tube; Syn4 was added at $10^3$ copies, Syn2 was added at $10^4$ copies, and Syn3 was added at $10^5$ copies per reaction. The Cp values from these templates were used to generate a composite internal standard curve for each reaction. An external standard curve was generated using a synthetic reference template *A. baumannii* reference template, also tested at the same concentrations as the "Syn" templates. The composite internal standard curve and the *A. baumannii* standard curves are very similar. The similar slope shows that the efficiencies are similar. It is expected that an unknown starting concentration of an *A. baumannii* sample can be predicted using the internal standard curve. However, because the y-intercept is shifted between the two curves, quantification of *A. baumannii* may benefit from a correction factor when using this internal standard curve.

Thus, the concentration of target organisms can be computed using the composite internal standard curve. Note that the internal standards are each at different known concentrations and are amplified in the same process as the target organisms. The methods illustratively employ cycle threshold (Ct) values (or alternatively a Cp value or other similar methods), which is the number of cycles of PCR required to obtain a fluorescence signal above the background fluorescence, for the target and internal standard, as determined experimentally. Other points may be used as well, such as using a first, second, or nth order derivative, illustratively as taught in U.S. Pat. No. 6,303,305, herein incorporated by reference in its entirety. Other points may be used as well, as are known in the art, and any such point may be substituted for Cp or Ct in any of the methods discussed herein. Illustratively, in a two-step multiplex system, the Cp value is determined in the nested second-stage reactions. However, in other embodiments, it is understood that the Cp may be determined as is appropriate for the amplification system. For example Cp may be determined in a single multiplex reaction or in a subsequent second-stage reaction by using oligonucleotide probes, each of which are specific for a quantification standard sequence and have a distinguishable fluorescent signal.

In an illustrative example where a single internal standard is used, the concentration of the target organism may be computed using the Ct of the target organism ($Ct_t$), the concentration and Ct of the internal standard (Concentration$_s$, $Ct_s$), and the target organism's efficiency (Efficiency$_t$) according to the following formula.

$$\text{Concentration}_t = \text{Concentration}_s * \text{Efficiency}_t^{(Ct_s - Ct_t)} \quad \text{[Equation 1]},$$

where the subscripts s and t represent the internal quantification standard and target organism, respectively, and $$\text{Efficiency}_t = 1 + \frac{\text{Efficiency as a percent}}{100}. \quad \text{[Equation 2]}$$

For example, the Efficiency variable for a target with 100% amplification each PCR cycle would equal 2. Note that the Efficiency is assumed to be predetermined and constant across a dynamic range. As discussed above, the efficiencies of the internal calibrators should all be similar, illustratively within 1%, within 2%, within 5%, or within 10% of each other. Similarly, the efficiencies of the targets should each be similar to that of the calibrators, illustratively within 2%, within 5%, within 10% or within 12% of the calibrators. It is understood that for precise quantification, efficiencies within a narrower range, illustratively within 1%, within 2%, or within 5% is desirable. However, for semi-quantitative or "binning" results (see below), a larger variation in efficiencies may be tolerated.

When two or more quantification standards are used, a standard quantification curve may be generated, illustratively using a least-squares regression line fit to the (Ct, log$_{10}$(Concentration)) data for the internal quantification standards, as illustrated in FIGS. 6A-6B. Illustratively, the regression fit is of the form:

$$\log_{10}(\text{Concentration})=(Ct-b)/a \quad \text{[Equation 3]},$$

where b is the intercept and represents the value of Ct when log$_{10}$(Concentration) is zero, and a is the slope which represents the degree to which Ct changes with a single unit change in template concentration (a function of efficiency). Given a computed Ct value for an unknown target, this formula gives the target concentration in Log$_{10}$ units. Other algorithms or equations may be applied, as needed, to improve the precision and accuracy of quantification. These may include adjustments required for platform-specific, matrix-specific, or assay-specific biases in extraction and/or amplification. These may also include algorithms that can account for differences in assay efficiencies in the separate steps of any multi-step amplification process. In some embodiments, the quantification standard curve may be non-linear, or may be linear only within a certain dynamic range. Illustratively, if there is a concentration-dependent variable slope, a sigmoidal dose-response curve may be used. Other non-linear curves are within the scope of this invention.

The method described above can be used for a target organism with an unknown concentration based on observed Ct values for the target and the regression equation for the standard curve generated using internal quantification standards. Ideally, all targets that are being quantified using this approach should have assays that have equivalent or similar PCR efficiencies as the internal quantification standards assays. However, there may be some variations in the slopes or intercepts of target assays standards curves. Given that target assays may have different amplification characteristics from the internal standards, assay specific correction factors can be used to adjust for systematic assay-specific bias to improve the accuracy of computed concentration of the unknown target. Illustratively, when a linear quantification curve is used, a may be corrected with a correction factor indicative of a different assay-specific efficiency (which changes the slope) or b may be corrected due to lack of optimal PCR conditions for a specific target that causes the target Ct to be delayed. Both corrections may be used where appropriate. In another example, illustratively when nested PCR is used, differences in b observed in PCR2 may be result of total outcome of the PCR1 assays, due to variations in the PCR1 efficiencies. In this case, the correction factor might be calculated as a function of the Ct values or be a constant depending on the desired quantification accuracy.

For example, a set of controlled experiments may be run with a known target organism concentration. If multiple replicates at a single concentration are used, then the assay specific correction factor may be computed as the average difference of the known concentration and the computed concentrations in Log$_{10}$ units. Illustratively, to obtain the corrected log concentration of the target organism, the assay specific correction factor may be added to the log concentration of the target organism (as computed above by the internal quantification standards method). Each target sequence in the multiplex assay illustratively will have its own correction (or no correction at all, if very similar to the composite standard curve).

Figure 8A:
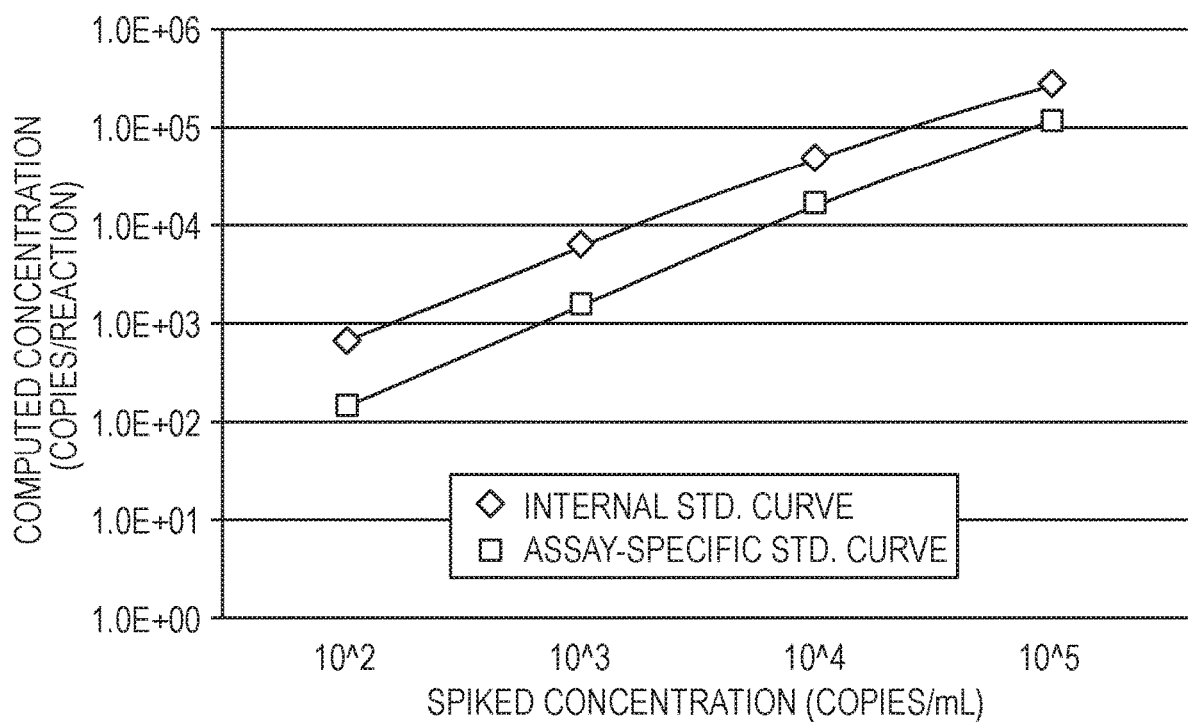
FIG. 8A shows the composite standard curve from quantification standards and the external standard curve specific for *A. baumannii*, without correction.
Figure 8B:
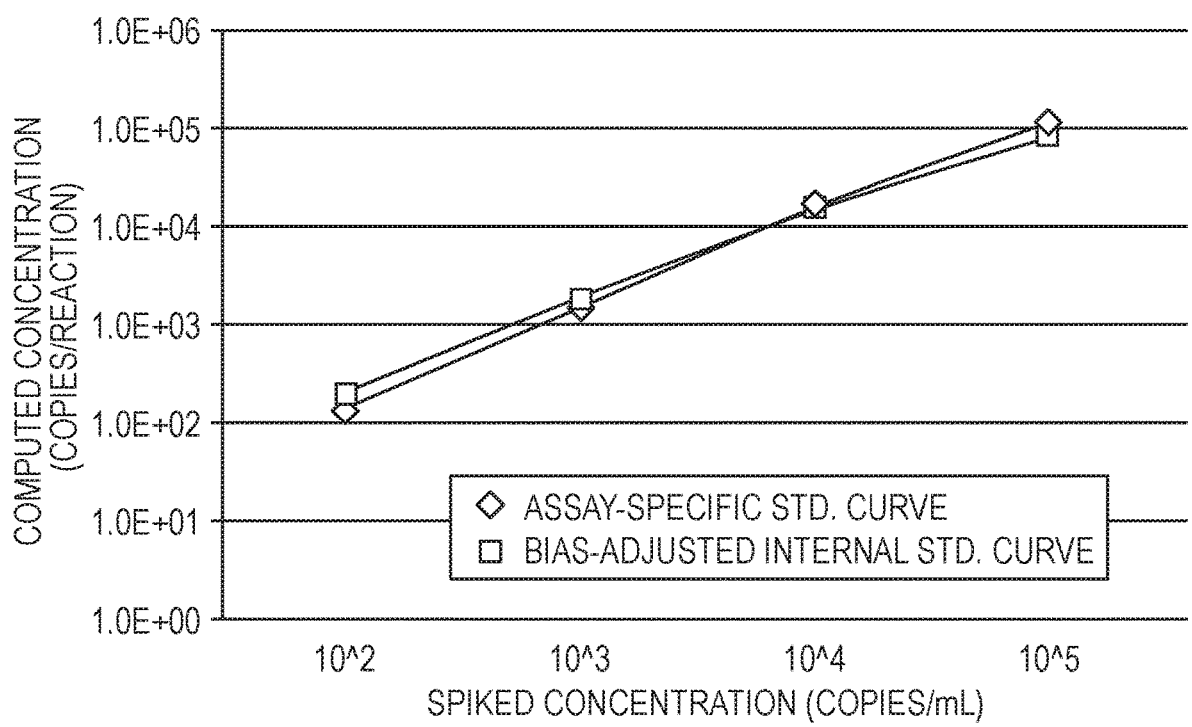
FIG. 8B shows the same data as FIG. 8A, with an assay-specific correction factor.

An experiment was set-up to compare quantification of a target organism computed by assay-specific standard curve to that computed by the composite internal standard curve. In this experiment, 10-fold serial dilutions of known quantities of *A. baumannii* genomic nucleic acid were multiplexed with internal quantification standards in bench-top reactions. An external assay-specific standard curve was also set-up as described above in reference to in FIG. 7. FIG. 8A shows the results of using the composite standard curve from quantification standards and the external standard curve specific for *A. baumannii*. If the composite standard curve is used without correction, there is an apparent systematic over-quantification (~0.5 log copy units) of the target organism (*A. baumannii*), whereas when the 0.5 log copy units correction is applied, the corrected assay-specific standard curve gives a fairly accurate estimate of the *A. baumannii* titer in the sample. FIG. 8B shows how this systematic bias in quantification can be corrected by applying an average assay-specific correction factor, generated as described above, to quantities computed by the internal standard curve method. Similar corrections may be made for each assay in the multiplex reaction.

In many embodiments, absolute quantification is not necessary, and semi-quantitative results may be sufficient. Results may be reported as absolute concentrations (with or without system error (illustratively 95% prediction interval)), or may be binned into one of a plurality of ranges, illustratively reporting a "high", "medium", or "low" concentration, each covering one or more orders of magnitude. It is understood that the number of bins may vary, as is appropriate with a specific assay, and any number of bins may be used. Also, the range of binning (orders of magnitude or other measures) for semi-quantitative results may be adjusted, as is appropriate for the specific example.

Example 4—Calibration in Inhibitory Sample Types

Inhibitory samples, illustratively inhibitory matrices, can affect extraction and amplification of internal quantification standards and target assays to more or less the same extent. Since the internal standards dynamically respond to matrix-driven effects in a way similar to the target sequences, they can also serve a normalization function. In this example, the three internal calibrators from Example 3 were used in the concentrations used above. TA-89 is a tracheal aspirate sample that was positive for *Streptococcus* spp. and was shown to have inhibitory properties as reflected in the considerably delayed Cps of the internal yeast RNA control in an illustrative FilmArray pouch used to test lower respiratory tract samples. TA-89 was used in three concentrations: as-is, diluted 2-fold, and diluted 10-fold. Each sample was spiked with *A. baumannii* at $10^6$ CFU/mL. As in Example 3, the three internal quantification standard templates at $10^3$, $10^4$ and $10^5$ copies/mL were also added to all sample aliquots. A PBS no-matrix control also spiked with the same concentration of *A. baumannii* and internal calibrators.

Figure 9:
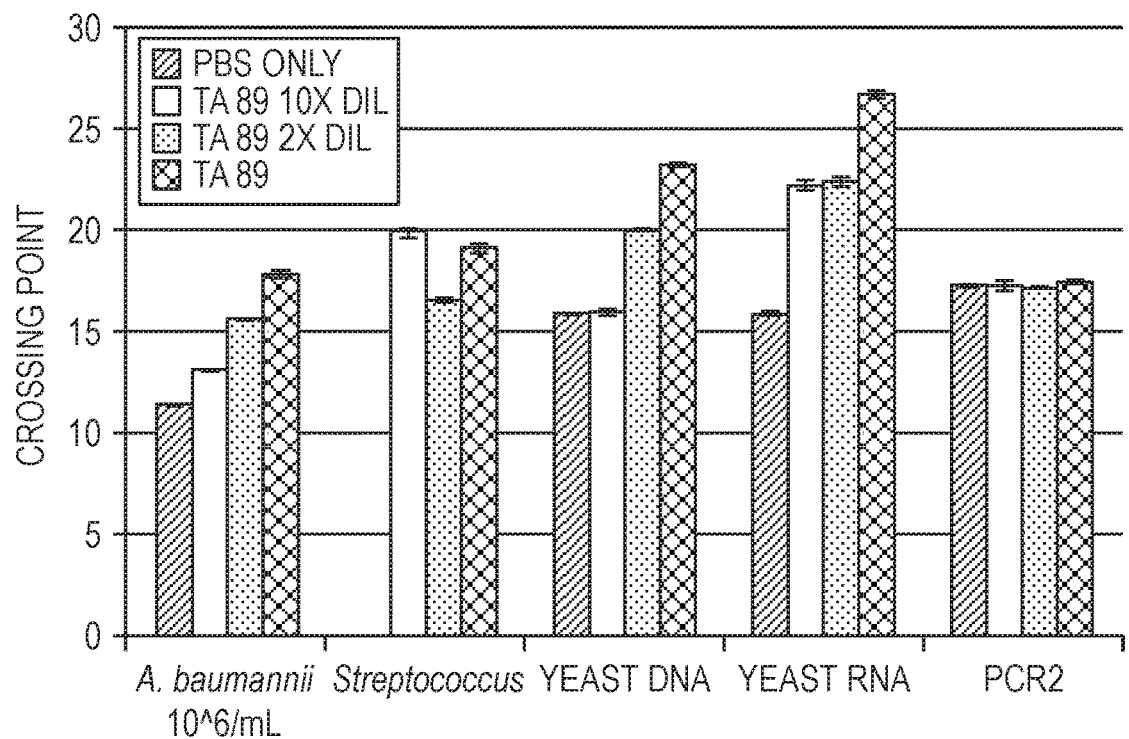
FIG. 9 shows the effect on Cp of an inhibitory matrix on various sample targets.
Figure 10:
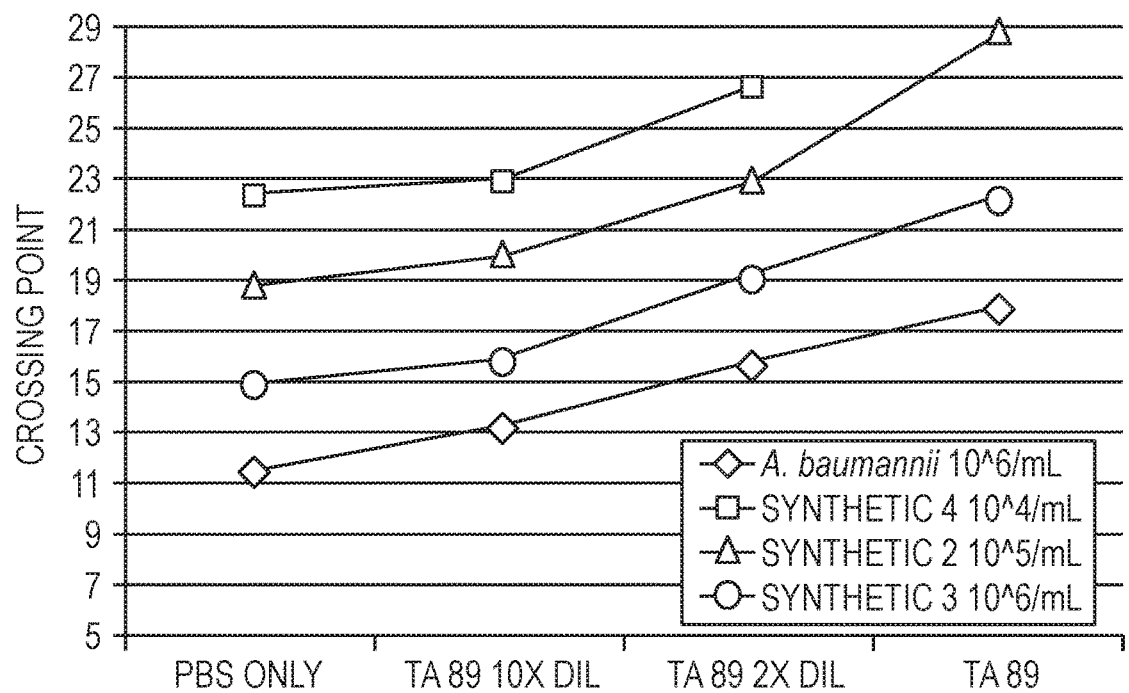
FIG. 10 plots the data from FIG. 9 for *A. baumannii*, where the x-axis represents increasing concentration of the inhibitory matrix and the y-axis is Cp.
Figure 11A:
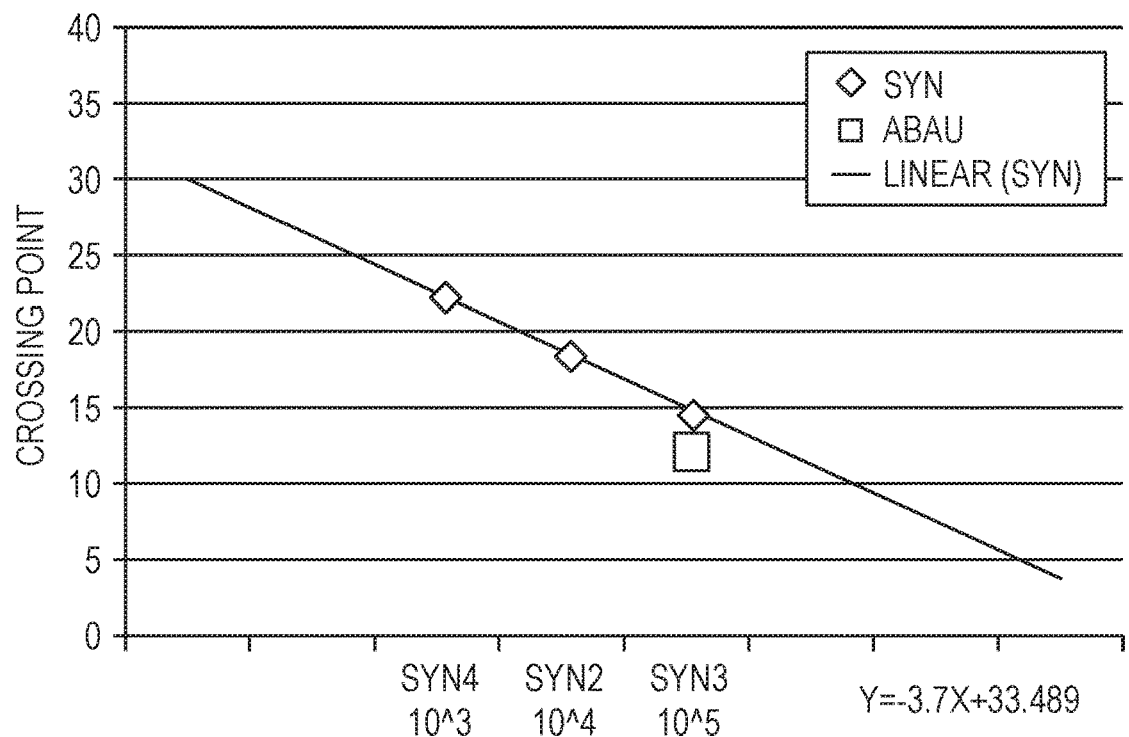
FIGS. 11A-11D show standard curves generated from three quantification standards, with a fixed amount of *A. baumannii*. The data in FIG. 11A were generated with a sample in PBS, the data in FIG. 11B were generated using a 10× dilution of an inhibitory matrix, the data in FIG. 11C were generated using a 2× dilution of an inhibitory matrix, and the data in FIG. 11D were generated using an inhibitory matrix without dilution.
Figure 11B:
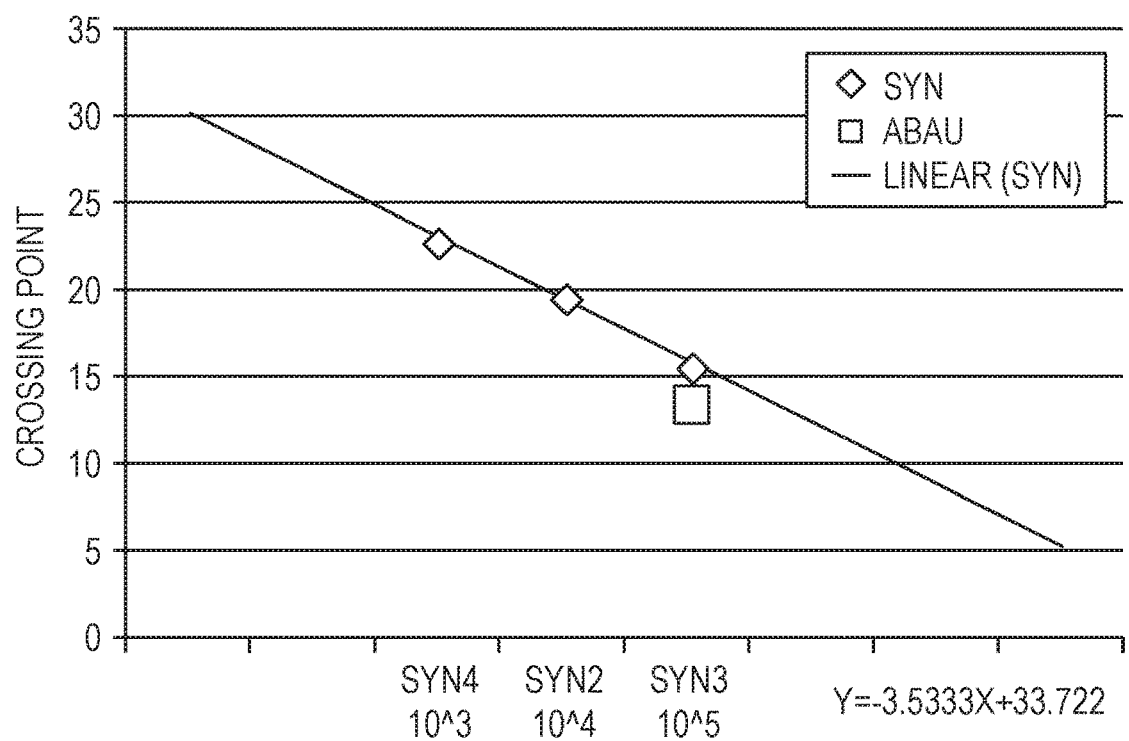
Figure 11C:
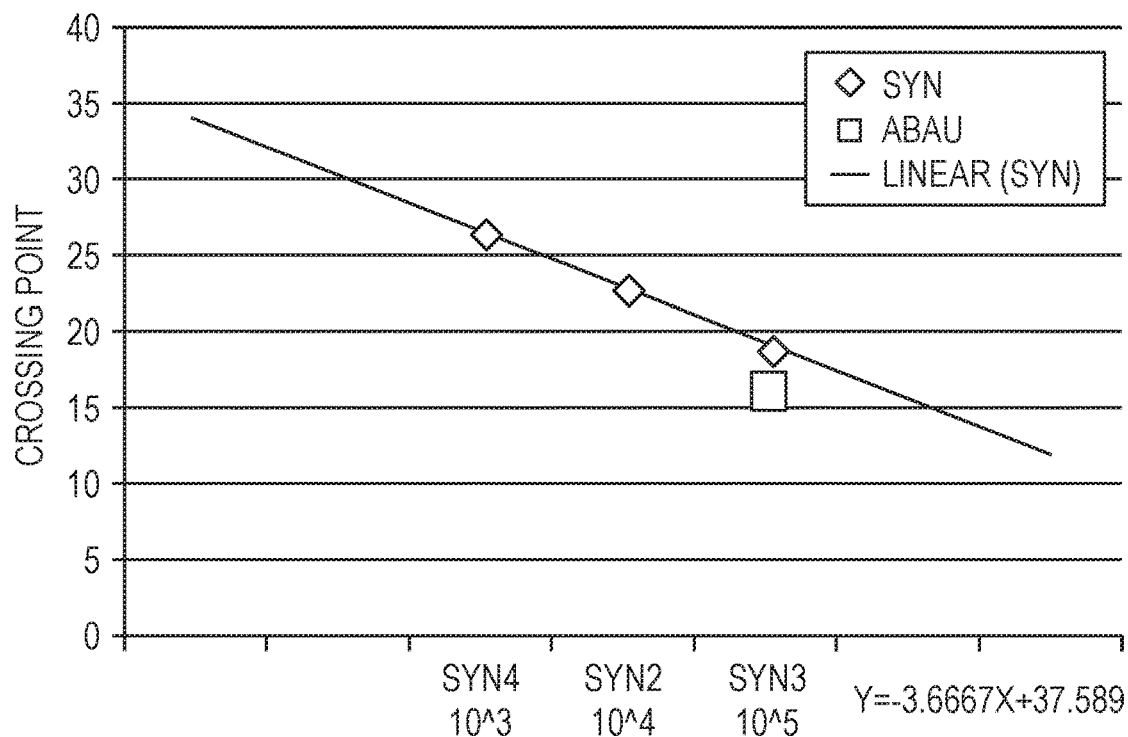
Figure 11D:
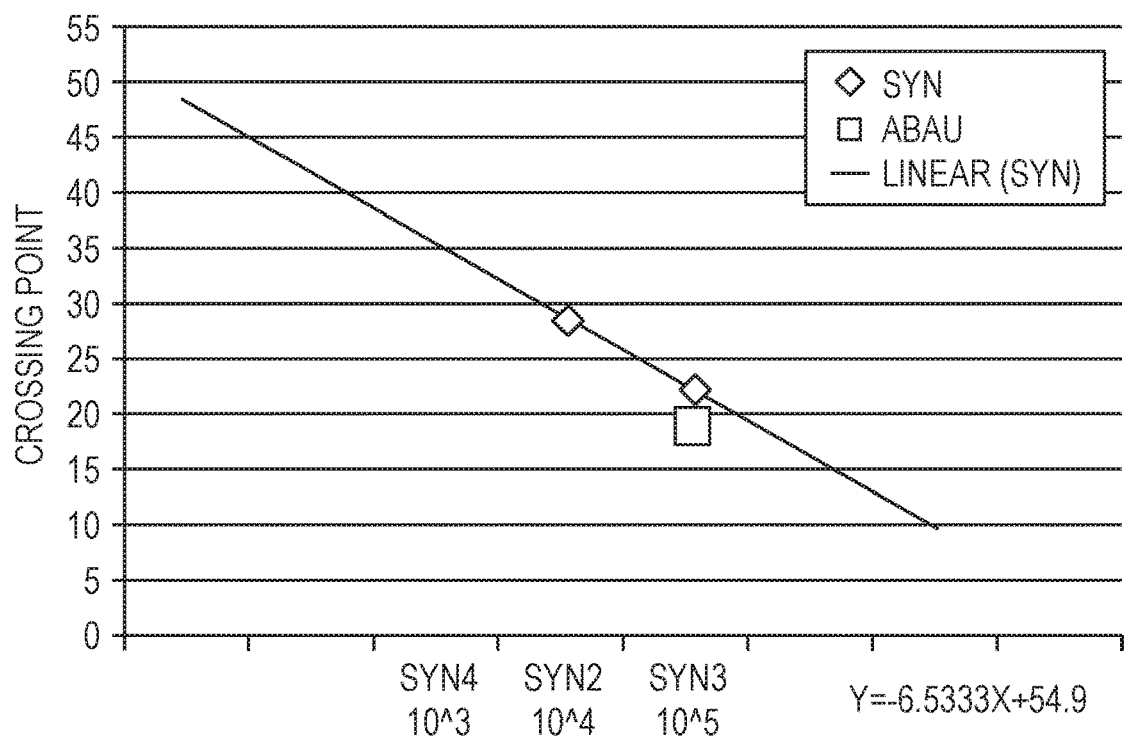

FIG. 9 shows the effect of dilution of an inhibitory matrix such as TA-89 on detection. The inhibitory matrix effect is visualized with the later Cps for *A. baumannii* in undiluted matrix and the trend to earlier Cps for *A. baumannii* is seen when the matrix is diluted, with the earliest Cp in the sample that did not contain the TA-89 matrix (PBS only). Despite differences in Ct values across matrix dilution, the amount of *A. baumannii* is the same in all dilutions of the matrix. In FIG. 10, one sees a similar trend in Cps for the quantification standards and the *A. baumannii* assays, with one of the quantification standards ($10^3$/mL) actually dropping out in the most inhibitory (undiluted) matrix.

In FIGS. 11A-D, the standard curves generated from the internal quantification standards for each of the TA-89 dilutions and the PBS no-matrix control are shown (diamonds). The Cp of *A. baumannii* (squares) is consistently earlier than the $10^5$/mL point in all sample matrices. Calculated concentrations for *A. baumannii* are shown below in Table 1. All predicted values are within three-fold of the actual concentration of $10^6$ CFU/mL. This demonstrates that the internal quantification standards and the *A. baumannii* template are all similarly affected by the inhibitory matrix, and generating a standard curve from the Cp or Ct values for the internal quantification standards provides a valuable tool for quantifying the target, even in inhibitory matrices.

TABLE 1

| Sample type | Template | y (Cp) | Predicted from std. curve (CFU/mL) |
|---|---|---|---|
| PBS (y = −3.7x + 33.48) | Syn4 10^3 | 21.01 | |
| | Syn2 10^4 | 16.13 | |
| | Syn3 10^5 | 14.22 | |
| | *A. baumannii* | 11.43 | 9.11E+05 |
| 10X (y = −3.533x + 33.72) | Syn4 10^3 | 22.93 | |
| | Syn2 10^4 | 19.97 | |
| | Syn3 10^5 | 15.87 | |
| | *A. baumannii* | 13.13 | 6.71E+05 |
| 2X (y = −3.666x + 37.58) | Syn4 10^3 | 26.6 | |
| | Syn2 10^4 | 22.9 | |
| | Syn3 10^5 | 19.27 | |
| | *A. baumannii* | 15.67 | 9.49E+05 |
| Undiluted (y = −6.533x + 54.9) | Syn4 10^3 | — | |
| | Syn2 10^4 | 28.77 | |
| | Syn3 10^5 | 22.23 | |
| | *A. baumannii* | 17.87 | 4.66E+05 |

Example 5—Quantification Using a Sample Processing Control

In this example, the use of a single synthetic quantification standard (QS) at a known concentration was compared to the use of a single microorganism at a known concentration, wherein the microorganism is also used as sample processing control (SPC), for the quantification of a pathogen (illustratively cytomegalovirus (CMV)). In this example, column-based extraction was used, and amplification was performed on a Bio-Rad CFX instrument, although it is understood that these methods and instruments are illustrative only.

The design of this experiment is shown in FIG. 12 and was performed in two steps:
  a first step including two parts: (A) the generation of a quantitative standard curve with the synthetic quantitative standard (QS), and (B) the calibration of a single natural sample processing control SPC with the quantitative standard curve generated therefrom.
  a second step corresponding to the quantification of the target nucleic acid (CMV) with the single natural quantification standard that is the SPC. In this illustrative example, the target nucleic acid is CMV and the SPC is *S. pombe*.

The experiment plan is as follows:
Illustratively, the first step was performed as follows:
Part A):
A first PCR mixture provided using the 5'nuclease real-time PCR technology including two primers and one probe, wherein the primers and probe are designed specifically to amplify and detect and quantify the target pathogen. Another PCR similar mixture is used, but designed for amplification and detection of the synthetic quantification standard. A third PCR similar mixture is used, designed for amplification and detection of the Sample Processing Control. It is understood that the 5'nuclease real-time PCR technology is illustrative only and that other detection means may be used.

Figure 13:
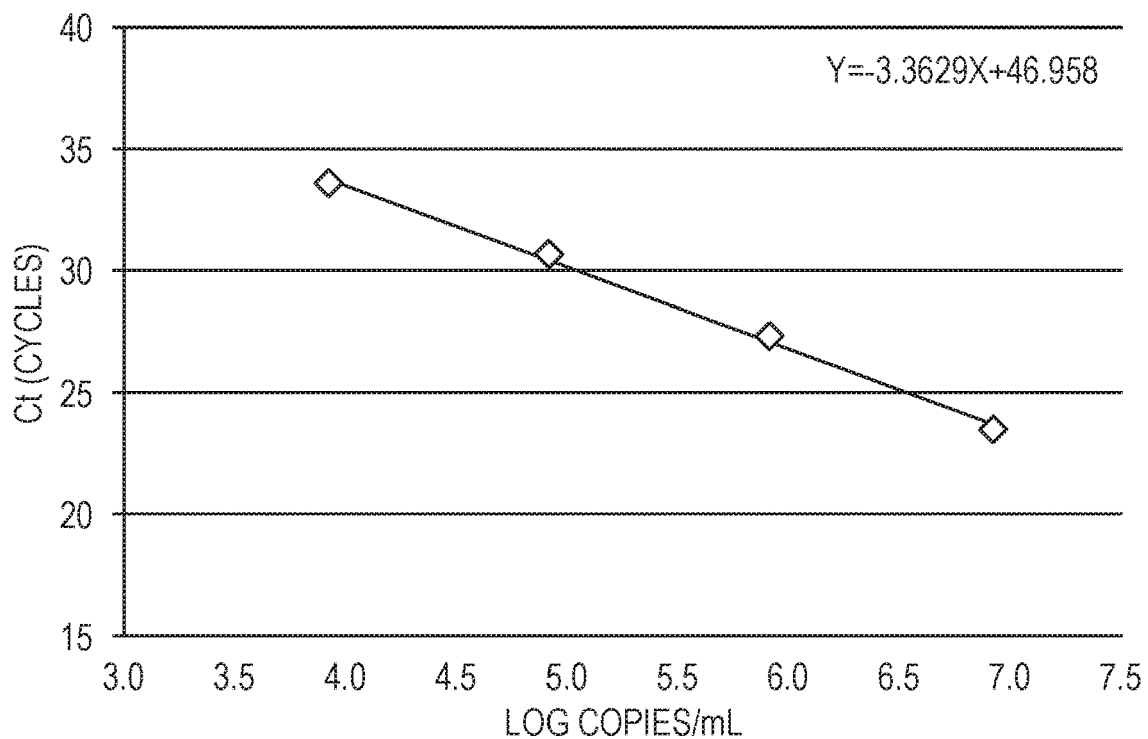
FIG. 13 shows a plot of the Cp across 4 dilutions of a synthetic quantification standard, used to generate a standard quantification curve.

In a first amplification run on the desired amplification platform, a range of 4 dilutions of a quantitative synthetic standard (QS 1 to QS4) was used to generate a standard quantification curve, using a regression line of the form:

$$Ct = (a * \text{Log}_{10} \text{Concentration}) + b \qquad \text{[Equation 4]}$$

or $$\text{Log}_{10}(\text{Concentration}) = (Ct - b)/a \qquad \text{[Equation 3],}$$

wherein a and b are as defined above.
The results obtained are shown in Table 2 below and illustrated in FIG. 13.

TABLE 2

| | Ct Value | Mean Ct Value | Log Copies/mL | Copies/mL |
|---|---|---|---|---|
| QS1 | 23.38 | 23.52 | 6,903 | 8,000,000 |
| | 23.52 | | | |
| | 23.66 | | | |
| QS2 | 27.30 | 27.33 | 5,903 | 800,000 |
| | 27.35 | | | |
| | 27.34 | | | |
| QS3 | 30.74 | 30.69 | 4,903 | 80,000 |
| | 30.61 | | | |
| | 30.72 | | | |
| QS4 | 33.62 | 33.61 | 3,903 | 8,000 |
| | 33.59 | | | |
| | 33.62 | | | |

Illustratively, in the same first run of the amplification platform, a range of 4 dilutions of the SPC microorganism *S. pombe* was tested. The results obtained are as shown in Table 3.

TABLE 3

| | id2maxd | Mean id2maxd | Log Copies/mL |
|---|---|---|---|
| SPC dil 1 | 28.503 | 28.56 | 5.47 |
| | 28.582 | | |
| | 28.596 | | |
| SPC dil 2 | 31.688 | 31.67 | 4.547 |
| | 31.655 | | |
| | 31.654 | | |
| SPC dil 3 | 34.053 | 33.93 | 3.88 |
| | 33.619 | | |
| | 34.106 | | |
| SPC dil 3 | neg | n/a | n/a |
| | neg | | |
| | neg | | |

Illustratively, Part B) was performed as follows:
The results obtained for the SPC *S. pombe* were calibrated against the standard quantification curve and the calibration factor is determined. The optimal SPC dilution (illustratively dilution 2), illustratively chosen to be in the middle of the relevant quantification range of the pathogens to detect, is selected on which the standard quantification curve will be placed with its pre-defined regression line slope. As discussed above, quantification by PCR frequently uses a standard curve approach. Also as discussed above, it has already been demonstrated that a standard curve could be stored, as parameters (intercept and slope), and imported on a single value (Ct) which allows one to adjust the quantification run by run, depending on the behavior of the SPC in the run.

In this example, the value 4.547 will be the value for $Log_{10}$ Concentration used to determine the equation of the next amplification runs when the SPC is used as the quantification standard for the quantification of the target CMV. Illustratively, the SPC may be called the adjuster or calibrator because it serves to adjust or calibrate the standard curve. At this step, one of the synthetic standards or one of the SPC dilutions could be used as the adjuster in the pre-defined regression line slope, with a factor of 4.903 for the use of the synthetic standard QS3, and a factor of 4.547 for the use of sample processing control dilution 2. The factor 4.547 is used to calculate the calibrated intercept, thereby allowing calculation of the CMV concentration with the SPC as quantitative standard using the regression line of the form:

$$Log_{10}(\text{Concentration}) = (Ct - b')/a \quad \text{[Equation 5]},$$

with a corresponding to the slope of the synthetic quantitative standard range and b' corresponding to the calibrated intercept and representing the theoretical value of Ct when $Log_{10}$(concentration) of SPC is zero when calibrated against the quantitative synthetic standard range.

Second Step:

A series of samples were then tested in parallel with the quantification standard QS3 and the sample processing control SPC *S. pombe* at a concentration of 80000 copies/mL: 4 dilutions of the reference CMV strain AD169 spiked in whole blood samples each in 4 replicates. Two whole blood samples obtained from QCMD (Quality Control Molecular Diagnostics) and 5 whole blood clinical samples were also used.

For the 23 samples, the concentration of CMV in the samples was determined by applying Equations 3 and 5.

The results were in the expected order of magnitude, as illustrated in Tables 4 and 5.

TABLE 4

|  | Ct CMV (cycles) | Ct QS3 (cycles) | log copies/mL CMV (based on QS3 quantification) |
|---|---|---|---|
| CMV1 | 27.38 | 30.19 | 5.74 |
|  | 27.43 | 30.19 | 5.73 |
|  | 27.40 | 30.24 | 5.75 |
|  | 27.45 | 29.99 | 5.66 |
| CMV2 | 30.22 | 30.30 | 4.93 |
|  | 30.34 | 30.46 | 4.94 |
|  | 30.54 | 30.31 | 4.83 |
|  | 30.42 | 30.47 | 4.92 |
| CMV3 | 33.00 | 30.66 | 4.21 |
|  | 33.13 | 30.69 | 4.18 |
|  | 33.19 | 30.23 | 4.02 |
|  | 33.22 | 30.52 | 4.10 |
| CMV4 | 35.66 | 30.64 | 3.41 |
|  | 35.32 | 30.63 | 3.51 |
|  | 35.75 | 30.57 | 3.36 |
|  | 34.88 | 30.50 | 3.60 |
| WB QCMD4 | 35.09 | 30.51 | 3.54 |
| WB QCMD7 | 33.09 | 30.56 | 4.15 |
| WB195 | 35.08 | 30.47 | 3.53 |
| WB206 | 31.04 | 30.50 | 4.74 |
| WB209 | 34.85 | 30.55 | 3.63 |
| WB400 | 32.92 | 30.56 | 4.20 |
| WB465 | 28.85 | 31.01 | 5.54 |

TABLE 5

|  | Ct SPC (cycles) | Ct CMV (cycles) | log copies/mL CMV (based on SPC quantification) | Corrected log copies/mL CMV |
|---|---|---|---|---|
| CMV1 | 30.19 | 27.38 | 5.38 | 5.84 |
|  | 30.00 | 27.43 | 5.31 | 5.77 |
|  | 30.39 | 27.40 | 5.44 | 5.90 |
|  | 30.04 | 27.45 | 5.32 | 5.78 |
| CMV2 | 30.40 | 30.22 | 4.60 | 5.06 |
|  | 30.05 | 30.34 | 4.46 | 4.92 |
|  | 30.17 | 30.54 | 4.44 | 4.90 |
|  | 30.11 | 30.42 | 4.46 | 4.92 |
| CMV3 | 30.19 | 33.01 | 3.71 | 4.17 |
|  | 30.45 | 33.13 | 3.75 | 4.21 |
|  | 30.11 | 33.19 | 3.63 | 4.09 |
|  | 30.19 | 33.22 | 3.64 | 4.10 |
| CMV4 | 30.21 | 35.66 | 2.93 | 3.39 |
|  | 30.41 | 35.32 | 3.09 | 3.55 |
|  | 30.37 | 35.75 | 2.95 | 3.41 |
|  | 29.90 | 34.88 | 3.07 | 3.53 |
| WB QCMD4 | 30.18 | 35.09 | 3.09 | 3.55 |
| WB QCMD7 | 29.98 | 33.09 | 3.62 | 4.08 |
| WB195 | 30.12 | 350.8 | 3.07 | 3.53 |
| WB206 | 30.14 | 31.03 | 4.28 | 4.74 |
| WB209 | 30.27 | 34.85 | 3.18 | 3.64 |
| WB400 | 30.41 | 32.92 | 3.80 | 4.26 |
| WB465 | 30.22 | 28.85 | 4.96 | 5.42 |

Using the sample processing control as a quantification standard in order to adjust standard curve parameters for the quantification takes advantage of the fact that this particle goes through all the same steps as a specimen and a potential pathogen infecting the test sample, but also has the same behavior as the pathogen to be detected.

The mean quantification gap between the quantification of CMV using the QS3 standard and the quantification of CMV using the SPC dil 2 is κ=0.46 Log. It is then used as a correction factor for the next runs to correct Log 10(concentration), as follows:

$$log_{10}(\text{concentration}_t) = log_{10}(\text{concentration}_s) + \kappa \quad \text{[Equation 6]}$$

wherein the subscripts $s$ and $t$ respectively represent the SPC and the target and κ is a correction factor previously determined for said target.

Thus the quantification of the pathogen can take into account a potential loss of yield and efficiency along the workflow, to become more accurate.

Figure 14:
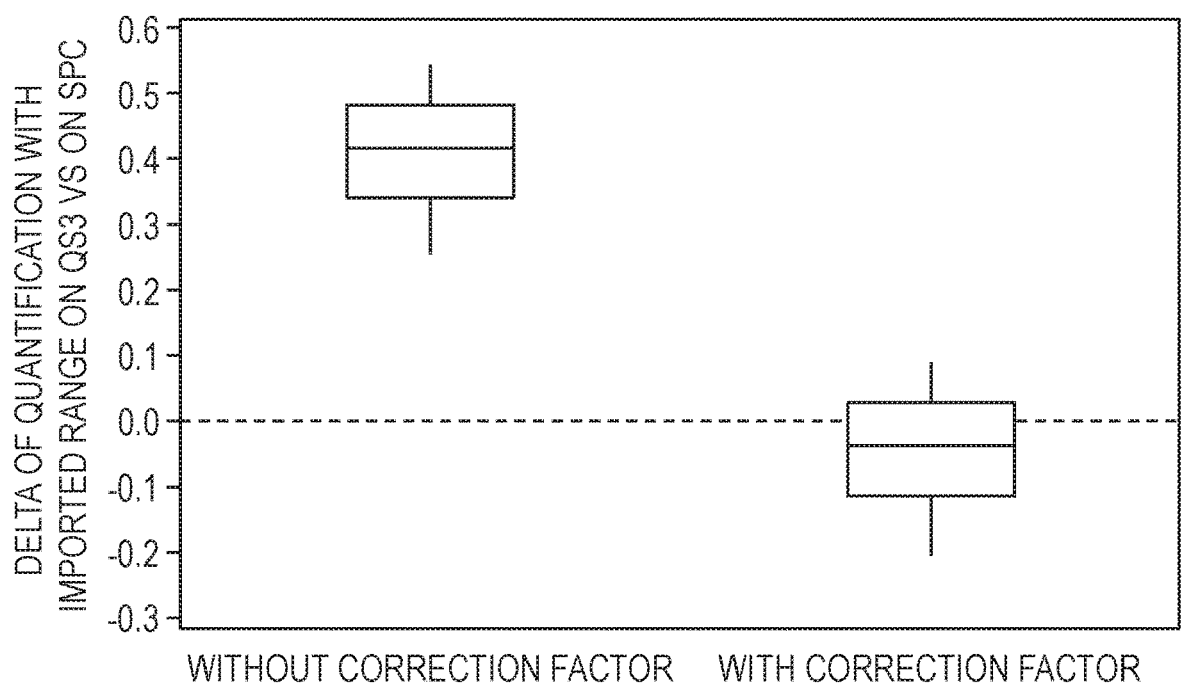
FIG. 14 is a box plot representation of the differences between quantification with a synthetic quantification standard (QS) and with the sample processing control (SPC), with or without application of the correction factor (0.46 Log in this illustrative example).

As shown in FIG. 14, the differences between quantification with QS and with SPC was 0.43 Log without applying the correction factor (κ=0.46) and −0.04 after correction.

It is understood that two or more sequences from the sample processing control that occur in different copy number could be used as internal quantification standards to generate a standard quantification curve that could be used to quantify targets in a multiplex assay. Similarly, at least two different sample processing controls may be used at different concentrations, again to generate a standard quantification curve that could be used as in the methods disclosed in Examples 2-4.

In addition to the quantification methods discussed herein, it is understood that any of the quantification standards described herein can be applied to test, compare, or optimize sample processing methods. The quantification standards can also be used to assist in estimating true titers of analytes (organisms) in the original sample, illustratively by factoring the loss during sample preparation.

In one illustrative example, the quantification standards can be applied to compare or optimize sample processing methods. Illustratively, the quantification standards can be used in one or more of the following processes: (1) optimization of various sample preparation sub-features, e.g., length of incubation steps, mag-bead collection time, wash steps, or elution steps; (2) comparison of extraction efficiency of different commercial or non-commercial sample preparation platforms, e.g., MagNA Pure®, QiaCube®, or Easy Mag™, to adopt an optimal platform; or (3) comparison of matrix effect on extraction, illustratively using the same platform, although cross-platform comparisons are also possible. For example, complex matrices such as sputum may cause greater hindrance to nucleic acid extraction than less complex matrices such as NPS or BAL. By sample preparation sub-feature modifications, sample preparation protocols can be developed that work equally well for multiple matrices.

For all of the above applications, illustratively comparisons may be done by adding one or more quantification standards (Template A) at a fixed quantity to the sample prior to sample preparation. Template A will then undergo all processes the sample is subjected to. The amount of Template A lost during sample preparation is expected be a good approximation of the amount of nucleic acid loss from the analytes in the sample. One or more second quantification standards (Template B) may then be added to the eluate at the same quantity as Template A. However, it is understood that a 1-to-1 ratio is not required and that other known amounts of Template B may be added. PCR will be performed on the eluate, and Cps of Template A will be compared to Cps of Template B. Given that none of Template B is lost during sample preparation, it is expected that Template B will amplify earlier. Illustratively, the protocol or platform that yields the smallest difference in Cps between Templates A and B may be a more efficient sample preparation method.

In another illustrative example, the quantification standards can be used to estimate true titers of analytes (e.g., organisms) in the original sample by factoring the loss during sample preparation. Thus, the difference between Templates A and B may be used for back-calculating true titer values in samples by estimating loss due to sample extraction efficiency issues. The magnitude of loss can be converted into a correction factor that can then be applied to the analyte quantities determined by traditional qPCR methods.

It is understood that Templates A and B may each be a single quantification standard, as in Example 5, or either or both may be combinations of quantification standards, illustratively at different concentrations, as in Examples 2-4.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A method of performing quantitative two-step amplification on a sample, comprising amplifying the sample in a first-stage multiplex amplification mixture, the amplification mixture comprising a plurality of target primers, each target primer configured to amplify a different target that may be present in the sample, the amplification mixture further comprising a plurality of internal quantification standard nucleic acids each of the quantification standards having a different sequence and each provided at a different known concentration and at least one quantification standard primer, the quantification standard primer configured to amplify quantification standard nucleic acids, dividing the first-stage amplification mixture into a plurality of second-stage individual reactions, a first group of the plurality of second-stage individual reactions each comprising at least one primer configured to further amplify one of the different targets that may be present in the sample, and a second group of the plurality of second-stage individual reactions each comprising at least one primer configured to further amplify one of the quantification standard nucleic acids, subjecting the plurality of second-stage individual reactions to amplification conditions to generate one or more target amplicons and a plurality of quantification standard amplicons, each quantification standard amplicon having an associated quantification standard Ct to thereby provide quantification standard Cts; and generating a standard curve from the quantification standard Cts.

2. The method of claim 1, further comprising quantifying each of the one or more targets using the standard curve.

3. The method of claim 2, wherein each of the targets is quantified using the standard curve generated using a least squares regression line fit to $$\log_{10}(\text{Concentration}) = (Ct-b)/a$$

where Ct is a cycle threshold measured for each target,
b, the intercept, represents the Ct value when the $\log_{10}$ (concentration) of the target is zero, and
a is the slope which represents the degree to which Ct changes with a single unit change in concentration.

4. The method of claim 3, wherein each of the targets is quantified using the least squares regression line and a correction factor.

5. The method of claim 2, wherein the standard curve is non-linear.

6. The method of claim 2, wherein the quantifying step reports a concentration.

7. The method of claim 2, wherein the quantifying step generates a concentration that falls within one of a plurality of ranges and reports that one range.

8. The method of claim 1, wherein the amplification is polymerase chain reaction (PCR) and each of the primers are provided in primer pairs.

9. The method of claim 8, wherein the amplification mixture comprises only one pair of quantification standard primers.

10. The method of claim 1, wherein the plurality of quantification standard nucleic acids includes at least two quantification standard nucleic acids.

11. The method of claim 1, wherein the quantification standard nucleic acids all have similar amplification efficiencies.

12. The method of claim 11, wherein all of the targets have similar amplification efficiencies.

13. The method of claim 1, wherein the internal quantification standard nucleic acids are naturally occurring sequences in the sample.

14. A method of performing quantitative amplification on a sample, comprising
amplifying the sample in an amplification mixture, the amplification mixture comprising a pair of target primers configured to amplify a target that may be present in the sample, the amplification mixture further comprising a plurality of quantification standard nucleic acids, each of the quantification standards having a different sequence and each provided at a different known concentration, and at least one pair of quantification standard primers, the quantification standard primers configured to amplify quantification standard nucleic acids to generate a plurality of amplification standard amplicons,
generating a standard curve from the quantification standard amplicons, and
quantifying the target nucleic acid using the standard curve.

15. The method of claim 14, wherein the amplification mixture further comprises a plurality of additional pairs of target primers configured to amplify a plurality of additional targets that may be present in the sample.

16. The method of claim 15, further comprising, subsequent to the amplifying step,
dividing the amplification mixture into a plurality of individual reactions, a first group of the plurality of individual reactions each comprising a pair of primers configured to further amplify one of the different targets that may be present in the sample, and a second group of the plurality of individual reactions each comprising a pair of primers configured to further amplify one of the quantification standard nucleic acids, and
subjecting the plurality of individual reactions to amplification conditions to generate one or more target amplicons and a plurality of quantification standard amplicons,
wherein the generating and quantifying steps take place subsequent to the subjecting step.

17. The method of claim 16, wherein each of the plurality of amplification standard amplicons has an associated Ct, and the generating step uses the Cts from the plurality of amplification standard amplicons.

18. The method of claim 17, wherein each of the targets is quantified using the standard curve generated using a least squares regression line fit to $$\log_{10}(\text{Concentration}) = (Ct-b)/a$$

where Ct is a cycle threshold measured for each target,
b, the intercept, represents the Ct value when the $\log_{10}$ (concentration) of the target is zero, and
a is the slope which represents the degree to which Ct changes with a single unit change in concentration.

19. The method of claim 18, wherein each of the targets is quantified using the least squares regression line and a correction factor.

20. The method of claim 17, wherein the quantifying step reports a concentration.

21. The method of claim 17, wherein the quantifying step generates a concentration that falls within one of a plurality of ranges and reports that one range.

22. The method of claim 14, further comprising detecting amplification of each of the quantification standard nucleic acids using a label specific for that quantification standard nucleic acid.

23. The method of claim 22, wherein each of the labels is a distinguishable labeled probe.

24. The method of claim 14 wherein each of the plurality of quantification standard nucleic acids is provided to the amplification mixture in known amounts to also serve as process controls.

25. The method of claim 14, wherein the amplification mixture comprises only one pair of quantification standard primers.

26. The method of claim 14, wherein the quantification standard nucleic acids are naturally occurring sequences in the sample.

* * * * *

UNITED STATES PATENT AND TRADEMARK OFFICE
CERTIFICATE OF CORRECTION

PATENT NO. : 11,268,141 B2
APPLICATION NO. : 16/087724
DATED : March 8, 2022
INVENTOR(S) : Spaulding et al.

It is certified that error appears in the above-identified patent and that said Letters Patent is hereby corrected as shown below:

On the Title Page

(73) Assignee: Please correct "Defence" to read -- Defense --

Signed and Sealed this
Eleventh Day of April, 2023

Katherine Kelly Vidal
*Director of the United States Patent and Trademark Office*